(12) United States Patent
Bryan et al.

(10) Patent No.: US 7,709,010 B2
(45) Date of Patent: May 4, 2010

(54) PAPILLOMAVIRUS VACCINE COMPOSITIONS

(75) Inventors: Janine T. Bryan, Furlong, PA (US); Michelle K. Brownlow, Jamison, PA (US); Li Shi, Marlborough, MA (US); Danilo Casimiro, Harleysville, PA (US); William L. McClements, Doylestown, PA (US); Brian K. Meyer, New Britain, PA (US); Binghua Hu, Audubon, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 7 days.

(21) Appl. No.: 12/074,783

(22) Filed: Mar. 6, 2008

(65) Prior Publication Data

US 2008/0248062 A1 Oct. 9, 2008

Related U.S. Application Data

(60) Provisional application No. 60/906,147, filed on Mar. 9, 2007.

(51) Int. Cl.
*A61K 45/00* (2006.01)
(52) U.S. Cl. .................................. 424/278.1
(58) Field of Classification Search ....................... None
See application file for complete search history.

(56) References Cited

U.S. PATENT DOCUMENTS

| | | | |
|---|---|---|---|
| 6,251,678 B1 * | 6/2001 | Volkin et al. | 436/8 |
| 6,352,697 B1 | 3/2002 | Cox et al. | |
| 6,372,227 B1 | 4/2002 | Garcon et al. | |
| 6,506,386 B1 | 1/2003 | Friede et al. | |
| 6,544,518 B1 * | 4/2003 | Friede et al. | 424/184.1 |
| 6,573,237 B2 * | 6/2003 | Rinella, Jr. | 514/2 |
| 6,846,489 B1 | 1/2005 | Garcon et al. | |
| 7,217,419 B2 | 5/2007 | Wettendorff | |

FOREIGN PATENT DOCUMENTS

| EP | 1 769 806 A2 | 4/2007 |
|---|---|---|
| WO | WO 2005/097821 A1 | 10/2005 |

OTHER PUBLICATIONS

Baker, T. et al. "Structures of bovine and human papillomaviruses Analysis by cryoelectron microscopy and three-dimensional image reconstruction", Biophysical Journal, 1991, vol. 60, pp. 1445-1456.
Barr, I. et al. "ISCOMS (immunostimulating complexes): The first decade", Immunology and Cell Biology, 1996, vol. 74, pp. 8-25.
Baylor, N. et al. "Aluminum salts in vaccines—US perspective", Vaccine, 2002, vol. 20, pp. S18-S23.
Bryan, J. "Developing an HPV vaccine to prevent cervical cancer and genital warts", Vaccine, 2007, vol. 25, pp. 3001-3006.
Caulfield, M. et al. "Effect of Alternative Aluminum Adjuvants on the Absorption and Immunogenicity of HPV16 L1 VLPs in Mice", Human Vaccines, 2007, vol. 3, pp. 139-146.
Harper, D. et al. "Efficacy of a bivalent L1 virus-like particle vaccine in prevention of infection with human papillomavirus types 16 and 18 in young women: a randomised controlled trial", The Lancet, 2004, vol. 364, pp. 1757-1765.
Klein, J. et al. "Analysis of Aluminum Hydroxyphosphate Vaccine Adjuvants by $_{27}$Al MAS NMR", Journal of Pharmaceutical Sciences, 2000, vol. 89, pp. 311-321.
Koutsky, L. et al. "A Controlled Trial of a Human Papillomavirus Type 16 Vaccine", The New England Journal of Medicine, 2002, vol. 347, pp. 1645-1651.
Lindblad, E. "Aluminium compounds for use in vaccines", Immunology and Cell Biology, 2004, vol. 82, pp. 497-505.
McMurray, H. et al. "Biology of human papillomaviruses", International Journal of Experimental Pathology, 2001, vol. 82, pp. 15-33.
Meyer, B. et al. "Antimicrobial Preservative Use in Parenteral Products: Past and Present", Journal of Pharmaceutical Sciences, 2007, vol. 96, pp. 3155-3167.
Ruiz, W. et al. "Kinetics and isotype profile of antibody responses in rhesus macaques induced following vaccination with HPV 6, 11, 16 and 18 L1-virus-like particles formulated with or without Merck aluminum adjuvant", Journal of Immune Based Therapies and Vaccines, 2005, vol. 3:2, pp. 1-11.
Schiffman, M. et al. "Epidemiologic Evidence Showing That Human Papillomavirus Infection Causes Most Cervical Intraepithelial Neoplasia", Journal of the National Cancer Institute, 1993, vol. 85, pp. 958-964.
Schiller, J. et al. "Developing HPV virus-like particle vaccines to prevent cervical cancer: a progress report", Journal of Clinical Virology, 2000, vol. 19, pp. 67-74.
Shank-Retzlaff, M. et al. "Evaluation of the Thermal Stability of Gardasil", Human Vaccines, 2006, vol. 2:4, pp. 147-154.
Shi, L. et al. "Gardasil: Prophylactic Human Papillomavirus Vaccine Development—From Bench Top to Bed-side", Clinical Pharmacology & Therapeutics, 2007, vol. 81, pp. 259-264.

(Continued)

*Primary Examiner*—Ali R. Salimi
(74) *Attorney, Agent, or Firm*—Alysia A. Finnegan; Sheldon O. Heber

(57) ABSTRACT

The present invention relates to pharmaceutical compositions comprising virus-like particles (VLPs) of HPV, said VLPs adsorbed to an aluminum adjuvant, and an ISCOM-type adjuvant comprising a saponin, cholesterol, and a phospholipid. In preferred embodiments, the aluminum adjuvant comprises amorphous aluminum hydroxyphosphate sulfate. Another aspect of the invention provides multi-dose HPV vaccine formulations comprising HPV VLPs and an antimicrobial preservative selected from the group consisting of: m-cresol, phenol and benzyl alcohol. Also provided are methods of using the disclosed pharmaceutical compositions and formulations to induce an immune response against HPV in a human patient and to prevent HPV infection.

16 Claims, 9 Drawing Sheets

OTHER PUBLICATIONS

Skene, C. et al. "Saponin-adjuvanted particulate vaccines for clinical use", Methods, 2006, vol. 40, pp. 53-59.

Villa, L. et al. "Immunologic responses following administration of a vaccine targeting human papillomavirus Types 6, 11, 16, and 18", Vaccine, 2006, vol. 24, pp. 5571-5583.

Frazer et al. "Phase 1 study of HPV16-specific immunotherapy with E6E7 fusion protein and ISCOMATRIXadjuvant in women with cervical intraepithelial neoplasia", Vaccine, 2004, vol. 23, pp. 172-181.

Giannini et al. "Enhanced humoral and memory B cellular immunity using HPV 16/18 L1 VLP vaccine formulated with the MPL/aluminium salt combination (AS04) compared to aluminium salt only", Vaccine, 2006, vol. 24, pp. 5937-5949.

Lam et al. "The Effect of Benzyl Alcohol on Recombinant Human Interferon-•"Pharmaceutical Research, 1997, vol. 14, pp. 725-729.

Maa et al. "Aggregation of recombinant human growth hormone induced by phenolic compounds", International Journal of Pharmaceutics, 1996, vol. 140, pp. 155-168.

Mach et al. "Disassembly and Reassembly of Yeast-Derived Recombinant Human Papillomavirus Virus-like Particles (HPV VLPs)", Journal of Pharmaceutical Sciences, 2006, vol. 95, pp. 2195-2206.

Remmele et al, "Interleukin-1 Receptor (IL-1R) Liquid Formulation Development Using Differential Scanning Calorimetry", Pharmaceutical Research, 1998, vol. 15, pp. 200-208.

Shi et al. "Stabilization of Human Papillomavirus Virus-Like Particles by Non-Ionic Surfactants", Journal of Pharmaceutical Sciences, 2005, vol. 94, pp. 1538-1551.

Stewart T. et al. "ISCOMATRIXadjuvant: an adjuvant suitable for use in anticancer vaccines", Vaccine, 2004, vol. 22, pp. 3738-3743.

Villa et al. "Prophylactic quadrivalent human papillomavirus (types 6, 11, 16 and 18) L1 virus-like particle vaccine in young women: a randomised double-blind placebo-controlled multicentre phase II efficacy trial", The Lancet Oncology, 2005, vol. 6, pp. 271-278.

Villa et al. "High sustained efficacy of a prophylactic quadrivalent human papillomavirus types 6/11/16/18 L1 virus-like particle vaccine through 5 years of follow-up", British Journal of Cancer, 2006, vol. 95, pp. 1459-1466.

Zhang et al. "Mechanism for Benzyl Alcohol-Induced Aggregation of Recombinant Human Interleukin-1 Receptor Antagonist in Aqueous Solution", Journal of Pharmaceutical Sciences, 2004, vol. 93, pp. 3076-3089.

* cited by examiner

| HPV-Type Study Time Point | GARDASIL™ (N=15) | | | Octavalent HPV L1 VLP Vaccine With AAHS/15 mcg IMX (N=30) | | | Octavalent HPV L1 VLP Vaccine With AAHS/30 mcg IMX (N=30) | | |
|---|---|---|---|---|---|---|---|---|---|
| | n | GMT (mMU/mL) | 95% CI | n | GMT (mMU/mL) | 95% CI | n | GMT (mMU/mL) | 95% CI |
| Anti-HPV 6 | | | | | | | | | |
| Day 1 | 14 | <20 | (<20, <20) | 25 | <20 | (<20, <20) | 22 | <20 | (<20, <20) |
| Month 03 | 14 | 875.4 | (467.7, 1,638.5) | 24 | 1,671.4 | (1,217.0, 2,295.3) | 22 | 2,892.7 | (1,997.8, 4,188.5) |
| Month 07 | 14 | 1,311.6 | (815.5, 2,109.5) | 25 | 2,116.6 | (1,654.3, 2,708.2) | 22 | 4,784.7 | (3,741.5, 6,118.8) |
| Anti-HPV 11 | | | | | | | | | |
| Day 1 | 14 | <20 | (<20, <20) | 25 | <20 | (<20, <20) | 22 | <20 | (<20, <20) |
| Month 03 | 14 | 1,453.0 | (846.6, 2,493.6) | 24 | 1,626.2 | (1,194.5, 2,213.8) | 22 | 2,197.1 | (1,685.7, 2,863.8) |
| Month 07 | 14 | 2,010.7 | (1,280.3, 3,157.9) | 25 | 2,508.3 | (1,964.4, 3,202.8) | 22 | 3,921.6 | (2,964.4, 5,188.0) |
| Anti-HPV 16 | | | | | | | | | |
| Day 1 | 14 | <20 | (<20, <20) | 23 | <20 | (<20, <20) | 25 | <20 | (<20, <20) |
| Month 03 | 14 | 1,611.0 | (832.2, 3,118.5) | 22 | 2,625.9 | (1,977.3, 3,487.2) | 24 | 4,302.8 | (3,189.3, 5,805.0) |
| Month 07 | 14 | 2,517.8 | (1,790.2, 3,540.9) | 23 | 3,961.8 | (2,982.6, 5,262.4) | 25 | 7,029.4 | (5,089.3, 9,709.0) |
| Anti-HPV 18 | | | | | | | | | |
| Day 1 | 14 | <20 | (<20, <20) | 27 | <20 | (<20, <20) | 26 | <20 | (<20, <20) |
| Month 03 | 14 | 197.9 | (107.7, 363.7) | 26 | 519.1 | (393.6, 684.6) | 25 | 924.2 | (581.8, 1,468.0) |
| Month 07 | 14 | 540.3 | (318.1, 917.6) | 27 | 1,303.9 | (946.6, 1,796.1) | 26 | 2,276.7 | (1,450.8, 3,572.8) |

FIG. 3

| HPV-Type Study Time Point | GARDASIL™ (N=15) | | | Octavalent HPV L1 VLP Vaccine With AAHS/60 mcg IMX (N=30) | | | Octavalent HPV L1 VLP Vaccine With AAHS/120 mcg IMX (N=30) | | |
|---|---|---|---|---|---|---|---|---|---|
| | n | GMT (mMU/mL) | 95% CI | n | GMT (mMU/mL) | 95% CI | n | GMT (mMU/mL) | 95% CI |
| Anti-HPV 6 Day 1 Month 03 | 14 14 | <20 1,667.7 | (<20, <20) (1,057.2, 2,630.7) | 26 25 | <20 2,615.3 | (<20, <20) (1,970.2, 3,471.7) | 26 25 | <20 4,296.5 | (<20, <20) (3,442.4, 5,362.6) |
| Anti-HPV 11 Day 1 Month 03 | 14 14 | <20 2,275.7 | (<20, <20) (1,665.3, 3,109.8) | 26 25 | <20 2,439.1 | (<20, <20) (1,996.7, 2,979.5) | 26 25 | <20 3,365.0 | (<20, <20) (2,624.5, 4,314.3) |
| Anti-HPV 16 Day 1 Month 03 | 15 15 | <20 1,969.2 | (<20, <20) (1,296.5, 2,991.0) | 28 27 | <20 4,992.1 | (<20, <20) (3,795.2, 6,566.5) | 23 22 | <20 7,282.4 | (<20, <20) (5,836.4, 9,086.8) |
| Anti-HPV 18 Day 1 Month 03 | 15 15 | <20 336.3 | (<20, <20) (217.0, 521.2) | 28 27 | <20 1,326.0 | (<20, <20) (936.3, 1,878.0) | 29 28 | <20 2,170.8 | (<20, <20) (1,578.4, 2,985.4) |

FIG.4

| Sample | T=0 | 4°C 6 M | 37°C 1 M | 37°C 3 M | 37°C 6 M |
|---|---|---|---|---|---|
| Type 6 | | | | | |
| HPV octavalent solution | 39.5 | 41.8 | 38.5 | 36.9 | 3.9 |
| HPV octavalent solution + IMX | 40.7 | 36.5 | 39.7 | 31.4 | 5.2 |
| HPV octavalent + MAA | 45.1 | 38.9 | 45.2 | 43.5 | 36.7 |
| HPV octavalent + MAA + IMX | 47.4 | 39.1 | 44.6 | 42.1 | 36.8 |
| Type 11 | | | | | |
| HPV octavalent solution | 69.6 | 78.4 | 71.8 | 61.4 | 11.8 |
| HPV octavelent solution + IMX | 78.0 | 77.7 | 71.2 | 55.8 | 17.0 |
| HPV octavalent + MAA | 85.3 | 90.8 | 82.0 | 72.0 | 62.5 |
| HPV octavalent + MAA + IMX | 94.6 | 96.0 | 78.3 | 71.8 | 62.6 |
| Type 16 | | | | | |
| HPV octavalent solution | 70.0 | 84.0 | 61.6 | 53.7 | 12.8 |
| HPV octavelent solution + IMX | 69.1 | 76.6 | 65.7 | 49.8 | 16.6 |
| HPV octavalent + MAA | 80.7 | 81.0 | 76.6 | 47.7 | 61.3 |
| HPV octavalent + MAA + IMX | 76.7 | 85.2 | 75.0 | 48.6 | 68.7 |
| Type 18 | | | | | |
| HPV octavalent solution | 30.9 | 36.6 | 31.4 | 25.8 | 5.3 |
| HPV octavelent solution + IMX | 31.2 | 38.5 | 29.1 | 21.7 | 9.7 |
| HPV octavalent + MAA | 36.3 | 44.1 | 37.9 | 33.5 | 36.3 |
| HPV octavalent + MAA + IMX | 34.0 | 43.7 | 38.9 | 33.2 | 36.8 |
| Type 31 | | | | | |
| HPV octavalent solution | 37.0 | 41.5 | 33.7 | 22.5 | 1.6 |
| HPV octavelent solution + IMX | 38.5 | 36.6 | 32.3 | 17.8 | 1.6 |
| HPV octavalent + MAA | 44.4 | 45.7 | 38.0 | 31.3 | 29.8 |
| HPV octavalent + MAA + IMX | 45.1 | 42.8 | 37.7 | 31.9 | 30.9 |
| Type 45 | | | | | |
| HPV octavalent solution | 38.3 | 39.1 | 34.3 | 28.7 | 5.5 |
| HPV octavelent solution + IMX | 39.9 | 34.8 | 32.2 | 27.0 | 10.1 |
| HPV octavalent + MAA | 42.6 | 41.1 | 37.7 | 33.2 | 31.0 |
| HPV octavalent + MAA + IMX | 42.6 | 39.1 | 37.3 | 32.4 | 31.2 |
| Type 52 | | | | | |
| HPV octavalent solution | 38.8 | 39.0 | 37.9 | 30.1 | 10.6 |
| HPV octavelent solution + IMX | 35.7 | 40.2 | N/A | 28.1 | 14.9 |
| HPV octavalent + MAA | 42.6 | 48.3 | 42.9 | 35.8 | 40.3 |
| HPV octavalent + MAA + IMX | 44.0 | 48.7 | 42.8 | 35.7 | 48.2 |
| Type 58 | | | | | |
| HPV octavalent solution | 38.8 | 51.6 | 33.2 | 19.5 | 2.7 |
| HPV octavelent solution + IMX | 35.7 | 49.7 | 29.6 | 16.3 | 3.7 |
| HPV octavalent + MAA | 42.6 | 55.6 | 39.2 | 36.2 | 41.8 |
| HPV octavalent + MAA + IMX | 44.0 | 56.0 | 41.5 | 37.0 | 40.9 |

FIG.6

PAPILLOMAVIRUS VACCINE COMPOSITIONS

CROSS-REFERENCE TO RELATED APPLICATIONS

This application claims priority to U.S. Ser. No. 60/906,147, filed Mar. 9, 2007, which is herein incorporated by reference in its entirety.

FIELD OF THE INVENTION

The present invention relates generally to the prevention of human papillomavirus (HPV) infection. More specifically, the invention relates to pharmaceutical compositions and formulations comprising virus-like particles (VLPs) of HPV, said VLPs adsorbed to an aluminum adjuvant, and a second adjuvant comprising a saponin, cholesterol, and a phospholipid. The invention also relates to pharmaceutical compositions and formulations comprising HPV VLPs and an antimicrobial preservative. Further provided are methods of using the disclosed pharmaceutical composition and formulations.

BACKGROUND OF THE INVENTION

There are more than 80 types of human papillomavirus (HPV), many of which have been associated with pathologies ranging from benign proliferative warts to malignant carcinomas of the cervix (for review, see McMurray et al., *Int. J. Exp. Pathol.* 82(1): 15-33 (2001)). HPV types 6 and 11 are termed "low-risk" and are the HPV types which are most commonly associated with benign warts, nonmalignant condyloma acuminata and/or low-grade dysplasia of the genital or respiratory mucosa. Approximately 90% of genital warts are caused by these two HPV types. In contrast, HPV16 and HPV18 are termed "high-risk" HPV types because they are most frequently associated with in situ and invasive carcinomas of the cervix, vagina, vulva and anal canal. More than 70% of cervical carcinomas are caused by infections with HPV16 and HPV18. Together with the less prevalent oncogenic types HPV 31, -33, -45, -52 and -58, these types account for greater than 90% of cervical cancer (Schiffman et al., *J. Natl. Cancer Inst.* 85(12): 958-64 (1993)). Cervical cancer is the second most prevalent cause of cancer deaths in women worldwide.

Papillomaviruses are small (50-60 nm), nonenveloped, icosahedral DNA viruses that encode up to eight early (E1-E7) and two late (L1-L2) genes. The L1 protein is the major capsid protein and has a molecular weight of 55-60 kDa. Expression of the L1 protein or a combination of the L1 and L2 proteins in yeast, insect cells, mammalian cells or bacteria leads to self-assembly of virus-like particles (VLPs) (for review, see Schiller and Roden, in *Papillomavirus Reviews Current Research on Papillomaviruses*; Lacey, ed. Leeds, UK: Leeds Medical Information, pp 101-12 (1996)). VLPs are morphologically similar to authentic virions and are capable of inducing high titres of neutralizing antibodies upon administration into animals or humans. Because VLPs do not contain the potentially oncogenic viral genome, they present a safe alternative to the use of live virus in HPV vaccine development (for review, see Schiller and Hidesheim, *J. Clin. Virol.* 19: 67-74 (2000)). For this reason, the L1 and L2 genes have been identified as immunological targets for the development of prophylactic and therapeutic vaccines for HPV infection and disease.

VLP-based vaccines have proven to be effective at inducing immune responses in human patients vaccinated with bivalent HPV 16 and 18 (Harper et al. *Lancet* 364(9447): 1757-65 (2004)) and quadrivalent HPV 6, 11, 16, and 18 VLP-based vaccines (Villa et al. *Vaccine* 24: 5571-5583 (2006)). However, it is a common goal of vaccine development to augment the immune response to the desired antigen to induce long lasting protective immunity.

Co-administration of vaccines with compounds that can enhance the immune response against the antigen of interest, known as adjuvants, has been extensively studied. In addition to increasing the immune response against the antigen of interest, some adjuvants may be used to decrease the amount of antigen necessary to provoke the desired immune response or decrease the number of injections needed in a clinical regimen to induce a durable immune response and provide protection from disease.

Aluminum-based compounds were determined to possess adjuvant activity over 60 years ago (for review, see Lindblad, E. B. *Immunol. and Cell Biol.* 82: 497-505 (2004); Baylor et al. *Vaccine* 20: S18-S23 (2002)). Aluminum adjuvants are generally regarded as safe when used at appropriate dosages. Many have been approved for administration into humans by regulatory agencies worldwide.

While the mechanism of action of aluminum adjuvants is not completely understood, it is generally thought that for optimal immunostimulating effect, the targeted antigen should be adsorbed onto the aluminum in a vaccine preparation (see Lindblad, supra). When formulated in this manner, aluminum adjuvants are able to induce potent antibody ($T_H2$) responses against many antigens; but rarely stimulate cellular ($T_H1$) immune responses. With regards to HPV, it has been shown that an HPV 6, 11, 16 and 18 L1 VLP-based vaccine in which the VLPs were adsorbed to an aluminum adjuvant produced a significantly stronger immune response in rhesus macaques than the response resulting from a corresponding L1 VLP vaccine lacking aluminum (Ruiz et al., *Journal of Immune Based Therapies and Vaccines* 3(1): 2 (2005)). It is important to note that while significantly higher antibody titers resulted from the aluminum-adjuvanted vaccine relative to VLPs alone, the immune response was not qualitatively different as both adjuvanted and non-adjuvanted vaccines produced similar isotype profiles.

In order to develop prophylactic HPV vaccines with long-term efficacy, it would be advantageous to achieve higher magnitude immune responses comprising strong humoral as well as cellular immune responses. It would also be beneficial to develop a VLP-based vaccine that produces an immune response to HPV L1 this is sufficiently enhanced to allow a reduced number of vaccine injections relative to current prophylactic clinical schedules.

SUMMARY OF THE INVENTION

The present invention provides pharmaceutical compositions and formulations that can induce an immune response against HPV in a patient and can prevent infection of HPV in the patient, which is the most effective method of eliminating the morbidity and mortality associated with HPV. The present invention also provides methods of using the compositions and formulations provided herein.

In one aspect, the present invention is related to pharmaceutical compositions comprising VLPs of at least one type of HPV, an aluminum adjuvant, an ISCOM-type adjuvant, and a pharmaceutically acceptable carrier, such as an excipient, diluent, stabilizer, buffer, or alternative substance that is designed to facilitate administration of the composition in the desired amount to the patient; wherein said VLPs are comprised of recombinant L1 protein or recombinant L1+L2 proteins of HPV and wherein said VLPs are adsorbed to said aluminum adjuvant. The compositions provided herein may also contain additional physiologically acceptable components, such as buffer, normal saline or phosphate buffered saline, sucrose, other salts and/or polysorbate.

The present invention further provides HPV vaccine formulations comprising: (a) from about 10 µg to about 100 µg of HPV VLPs of at least one HPV type, wherein the HPV type is selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; said HPV VLPs comprised of recombinant L1 or recombinant L1+L2 protein of HPV; (b) from about 150 µg to about 600 µg of aluminum adjuvant; and (c) from about 10 µg to about 200 µg of an ISCOM-type adjuvant, said ISCOM-type adjuvant comprising a saponin, cholesterol, and a phospholipid; wherein said HPV VLPs are adsorbed onto said aluminum adjuvant.

In a specific embodiment of this aspect of the invention, the HPV vaccine formulation comprises (a) from about 20 µg to about 60 µg of VLPs of at least one HPV type; (b) from about 200 µg to about 300 µg of the aluminum adjuvant; and (c) from about 15 µg to about 120 µg of the ISCOM-type adjuvant.

In still other specific embodiments, the invention provides an HPV vaccine formulation comprising: (a) from about 20 µg to about 60 µg of VLPs of each of HPV types 6, 11, 16, 18, 31, 45, 52, and 58, said HPV VLPs comprised of recombinant L1 or recombinant L1+L2 protein of HPV; (b) from about 200 µg to about 300 µg of aluminum adjuvant; and (c) from about 30 µg to about 120 µg of an ISCOM-type adjuvant, said ISCOM-type adjuvant comprising a saponin, cholesterol, and a phospholipid; wherein said HPV VLPs are adsorbed onto said aluminum adjuvant.

In a further aspect of the invention, there are provided pharmaceutical compositions comprising HPV VLPs, an antimicrobial preservative selected from the group consisting of: m-cresol, phenol, and benzyl alcohol, and a pharmaceutically acceptable carrier. The antimicrobial preservative-containing HPV vaccine compositions may optionally comprise an aluminum adjuvant and an ISCOM-type adjuvant, as described, supra; however, HPV VLP compositions comprising an antimicrobial preservative without an adjuvant are also contemplated.

Also provided by the present invention is a method of inducing an immune response to HPV in a human patient comprising administering to the patient a pharmaceutical composition comprising HPV VLPs, an aluminum adjuvant, and an ISCOM-type adjuvant, said ISCOM-type adjuvant comprising a saponin, cholesterol, and a phospholipid; wherein said HPV VLPs are comprised of recombinant L1 protein or recombinant L1+L2 protein of HPV and wherein said VLPs are adsorbed to the aluminum adjuvant.

The present invention further relates to a method of preventing infection of a human patient by an HPV comprising administration of a pharmaceutical composition comprising recombinant HPV VLPs, aluminum adjuvant, and an ISCOM-type adjuvant to the patient, wherein said ISCOM-type adjuvant, wherein the HPV VLPs are comprised of recombinant L1 protein or recombinant L1+L2 protein of HPV and wherein said VLPs are adsorbed to the aluminum adjuvant.

As used throughout the specification and in the appended claims, the singular forms "a," "an," and "the" include the plural reference unless the context clearly dictates otherwise.

As used throughout the specification and appended claims, the following definitions and abbreviations apply:

The terms "HPV" and "PV" refer to human papillomavirus and papillomavirus, respectively.

The term "effective amount" means sufficient VLP vaccine composition is introduced to a patient to produce a desired effect such as inducing an immune response against HPV in the patient or preventing HPV infection. One skilled in the art recognizes that this level may vary.

The term "patient" refers to any human being that is to receive the HPV vaccines, or pharmaceutical compositions, described herein. As defined herein, a "patient" includes those already infected with HPV as well as those in which HPV infection is to be prevented.

A "disorder" is any condition that would benefit from treatment with the compositions of the present invention. Encompassed by the term "disorder" are any disorder or pathology that is associated with infection by HPV. The compositions of the present invention are intended for use as treatments or for prophylaxis of disorders or conditions characterized by HPV infection, including, but not limited to, benign warts, nonmalignant condyloma acuminata and/or low-grade dysplasia of the genital or respiratory mucosa, and in situ and invasive carcinomas of the cervix, vagina, vulva and anal canal.

"Formulation" refers to a single dose of vaccine, which can be included in any volume suitable for injection. In specific embodiments, a formulation is made in a 0.5 mL total volume. Unless otherwise stated, use of the term "formulation" applies to a single dose of vaccine, which can be delivered to a single patient in need thereof. The term "multi-dose" refers to an HPV formulation which contains more than one dose of vaccine, which can be administered to more than one patient.

"VLP" or "VLPs" mean(s) virus-like particle or virus-like particles.

"MAA" means Merck aluminum adjuvant. MAA is an amorphous aluminum hydroxyphosphate sulfate adjuvant. The term "MAA" is used interchangeably herein with the term "AAHS."

"cLIA" refers to a competitive Luminex (Luminex Corp., Austin Tex.) immunoassay, an example of which is described in U.S. Pat. No. 7,067,258 and in Opalka et al. *Clin Diagn Lab Immunol.* 10(1):108-15 (2003).

"GMT" refers to a geometric mean titer.

An "ISCOM-type adjuvant" is an adjuvant comprising an immune stimulating complex (ISCOM), which is comprised of a saponin, cholesterol, and a phospholipid, which together form a characteristic caged-like particle, having a unique spherical, caged-like structure that contributes to its function (for review, see Barr and Mitchell, *Immunology and Cell Biology* 74: 8-25 (1996)). This term includes both ISCOM adjuvants, which are produced with an antigen and comprise antigen within the ISCOM particle and ISCOM matrix adjuvants, which hollow ISCOM-type adjuvants that are produced without antigen. In preferred embodiments of the compositions and methods provided herein, the ISCOM-type adjuvant is an ISCOM matrix particle adjuvant, such as ISCOMATRIX®, which is manufactured without antigen (ISCOM® and ISCOMATRIX® are the registered trademarks of CSL Limited, Parkville, Australia).

BRIEF DESCRIPTION OF THE DRAWINGS

FIG. 3 shows a summary of anti-HPV 6, 11, 16 or 18 cLIA geometric mean titers (GMT) by vaccination group among human subjects who were seronegative to the relevant HPV type(s) at day 1 (Phase A results). A brief description of the clinical protocol is set forth in EXAMPLE 3.

FIG. 4 shows a summary of anti-HPV 6, 11, 16 or 18 cLIA geometric mean titers (GMT) by vaccination group among human subjects who were seronegative to the relevant HPV type(s) at day 1 (Phase B results). A brief description of the clinical protocol is set forth in EXAMPLE 3.

FIG. 6 shows the in vitro antigenicity of octavalent HPV solution and MAA samples with and without IMX determined by IVRP analysis (units/mL) (see EXAMPLES 4 and 6).

DETAILED DESCRIPTION OF THE INVENTION

Figure 1:
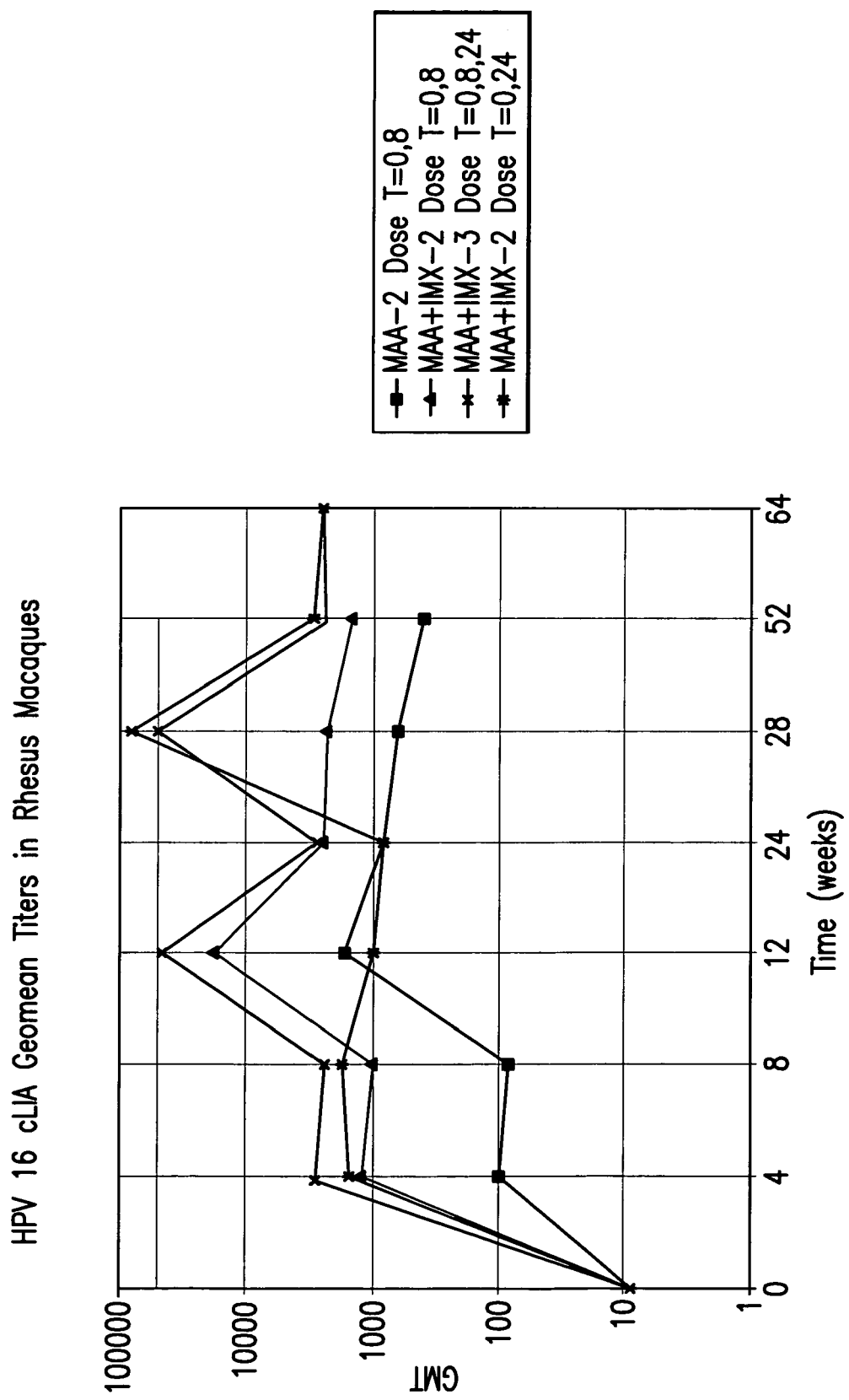
FIG. 1 shows the anti-HPV16 geometric mean titers (GMT) by vaccination group among rhesus macaques immunized with an experimental octavalent HPV VLP vaccine over time. The vaccines were adjuvanted either with MAA or MAA+IMX, according to the indicated immunization schedule and as described in EXAMPLE 1.

In accordance with this invention, it has been shown that HPV vaccine formulations comprising HPV VLPs of at least one HPV type, an ISCOM-type adjuvant and an aluminum adjuvant are able to provoke higher Ab titers to the targeted HPV types in animal models and in human patients when compared to VLP vaccines comprising aluminum adjuvant alone. To this end, HPV VLP vaccine formulations and pharmaceutical compositions are provided herein that comprise HPV VLPs which are adsorbed onto aluminum adjuvant in combination with an ISCOM-type adjuvant, as described in detail below.

In accordance with another aspect of the invention described herein, it has been shown that the addition of an antimicrobial preservative selected from the group consisting of: m-cresol, phenol, and benzyl alcohol, to pharmaceutical compositions and formulations comprising HPV VLPs is effective at reducing or eliminating microbes and does not negatively impact the structural and thermal stability of the VLPs at 2-8° C. Thus, the invention also relates to HPV vaccine formulations and pharmaceutical compositions comprising HPV VLPs and an antimicrobial preservative selected from the group consisting of: m-cresol, phenol and benzyl alcohol. The vaccine compositions according to this aspect of the invention may also include and ISCOM-type adjuvant and an aluminum adjuvant, as described above.

Virus-like particle-based vaccines have proven to be safe and effective at inducing immune responses against many types of HPV in human patients. VLPs can self-assemble when L1, the major capsid protein of human and animal papillomaviruses, is expressed in yeast, insect cells, mammalian cells or bacteria (for review, see Schiller and Roden, in *Papillomavirus Reviews: Current Research on Papillomaviruses*; Lacey, ed. Leeds, UK: Leeds Medical Information, pp 101-12 (1996)). Morphologically indistinct HPV VLPs can also be produced by expressing a combination of the L1 and L2 capsid proteins. VLPs are composed of 72 pentamers of L1 in a T=7 icosahedral structure (Baker et al., *Biophys. J.* 60(6): 1445-56 (1991)).

VLPs are morphologically similar to authentic virions and are capable of inducing high titres of neutralizing antibodies upon administration into an animal. Immunization of rabbits (Breitburd et al., *J. Virol.* 69(6): 3959-63 (1995)) and dogs (Suzich et al., *Proc. Natl. Acad. Sci. USA* 92(25): 11553-57 (1995)) with VLPs was shown to both induce neutralizing antibodies and protect against experimental papillomavirus infection. Additionally, immunization of adult women with HPV16 VLPs was shown to protect against HPV16 infection and HPV16 cervical intraepithelial neoplasia (Koutsky et al. *N. Engl. J. Med.* 347: 1645-51 (2002)). Because VLPs do not contain the potentially oncogenic viral genome and can self-assemble when expressed from a single gene, they present a safe alternative to the use of live virus in HPV vaccine development (for review, see Schiller and Hidesheim, J. Clin. Virol. 19: 67-74 (2000)).

As stated above, VLP-based vaccines have proven to be effective at inducing immune responses in many animal models and in human patients. However, a goal of vaccine development is often to induce higher antibody titers, leading to long lasting protective immunity. To this end, pharmaceutical compositions and vaccines comprising HPV VLPs of at least one HPV type, an ISCOM-type adjuvant and an aluminum adjuvant have been developed, as disclosed herein. Said pharmaceutical compositions and vaccines are able to provoke higher IgG Ab titers to the targeted HPV types than VLP vaccines comprising aluminum adjuvant alone. This combination can lead to the induction of long-lasting effective immunoprophylaxis against HPV infection, reduced antigen dosage, and immunization schedules comprising a decreased number of injections over time.

Thus, the present invention relates to pharmaceutical compositions and formulations comprising HPV virus-like particles, an aluminum adjuvant, an ISCOM-type adjuvant, and a pharmaceutically acceptable carrier, wherein said VLPs are comprised of recombinant L1 protein or recombinant L1+L2 proteins of HPV and wherein said VLPs are adsorbed to said aluminum adjuvant.

Any HPV VLP-based vaccine is suitable for use in the pharmaceutical compositions and methods of the present invention. Known HPV VLP vaccines can be modified to include both an aluminum adjuvant and an ISCOM-type adjuvant. Additionally, new vaccines can be developed according to the invention described herein that comprise at least one HPV type in the form of an HPV VLP adsorbed to an aluminum adjuvant in combination with an ISCOM-type adjuvant.

An exemplary HPV VLP vaccine is the Quadrivalent Human Papillomavirus (Types 6, 11, 16, 18) Recombinant Vaccine, which is referred to herein by its proprietary name GARDASIL® (see Bryan, J. T. *Vaccine* 25(16): 3001-6 (2007); Shi et al. *Clinical Pharmacology and Therapeutics* 81(2): 259-64 (2007)). GARDASIL® is a non-infectious recombinant, quadrivalent vaccine prepared from highly purified VLPs of the major capsid (L1) protein of HPV types 6, 11, 16, and 18. The L1 proteins are produced by separate fermentations in recombinant *Saccharomyces cerevisiae* and self-assembled into VLPs. In addition to VLPs, each GARDASIL® vaccine dose contains aluminum adjuvant (as amorphous aluminum hydroxyphosphate sulfate), sodium chloride, L-histidine, polysorbate 80, sodium borate, and water. Therefore, the present invention includes the combination of GARDASIL® with an ISCOM-type adjuvant, such as ISCOMATRIX® (CSL Ltd., Parkville, Australia).

In alternative embodiments of the invention, the pharmaceutical compositions and formulations comprise HPV VLP-based vaccines which are monovalent, bivalent, or trivalent. For example, pharmaceutical compositions comprising VLPs of HPV16 and/or HPV18, without the inclusion of other HPV VLP types, are included within the scope of the invention. Quadrivalent vaccines comprising different HPV VLPs than the HPV types included in GARDASIL® are also contemplated herein. For example, pharmaceutical compositions comprising VLPs of HPV types 31, 45, 52, and 58 are within the scope of this invention.

In additional embodiments, the pharmaceutical compositions comprise VLP-based vaccines with more than four different types of VLPs. In one preferred embodiment, the pharmaceutical composition comprises eight different HPV VLP types. A particularly preferred octavalent vaccine is described in EXAMPLES 1 and 2 and comprises HPV types 6, 11, 16, 18, 31, 45, 52, and 58. An alternative octavalent composition of the present invention comprises HPV types 6, 11, 16, 18, 31, 35, 45, and 58. Other octavalent HPV VLP vaccines are also contemplated herein; for example, HPV 33 may be substituted for HPV 31. Additional HPV VLPs may also be added to the vaccine formulations described herein, leading to HPV vaccines that are 9-valent, 10-valent, and so forth.

As stated above, the pharmaceutical compositions and formulations of the present invention comprise at least one HPV VLP type, such as HPV16 or 18. In preferred embodiments of the compositions disclosed herein, the vaccine further comprises VLPs of at least one additional HPV type. In particularly preferred embodiments, the at least one additional HPV type is selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82.

The pharmaceutical compositions of the present invention comprise HPV VLPs comprised of recombinant L1 or recombinant L1+L2 proteins of HPV. HPV L1 or L1+L2 protein can be expressed recombinantly by molecular cloning of L1 or L1+L2 DNA into an expression vector containing a suitable promoter and other appropriate transcription regulatory elements, and transferred into prokaryotic or eukaryotic host cells to produce recombinant protein. Techniques for such manipulations are fully described by Sambrook et al. (*Molecular Cloning: A Laboratory Manual*; Cold Spring Harbor Laboratory, Cold Spring Harbor, N.Y., (1989)), which is hereby incorporated by reference. VLPs can self-assemble when L1 protein is recombinantly expressed in a host cell.

The recombinant HPV L1 proteins of the present invention may be any full-length L1 protein sequence that can be found in nature or any mutated or truncated L1 protein that is capable of self-assembling into VLPs. L1 protein sequences for use in the present invention can be determined by isolating DNA from one or more clinical samples containing an HPV type of choice, determining the sequence of the HPV L1 DNA sequence, and translating the DNA sequence into an amino acid sequence using the genetic code. Many exemplary L1 sequences suitable for use in the present invention can be found in the literature. See, e.g., U.S. Pat. Nos. 5,820,870; 7,250,170; 7,276,243; and 5,437,951; Kirii et al. (*Virology* 185(1): 424-427 (1991)). Further L1 proteins that are useful in the compositions and formulations of the present invention include biologically active fragments and/or mutants of an HPV L1 sequence, including but not necessarily limited to amino acid substitutions, deletions, additions, amino terminal truncations and carboxy-terminal truncations, such that these mutations provide for L1 proteins or protein fragments that are capable of forming a VLP. See, e.g., International Publication WO2006/114312 and U.S. Pat. No. 6,599,508.

Appropriate host cells for the expression of recombinant HPV L1 or recombinant L1+L2 and subsequent self-assembly of VLPs include, but are not limited to yeast cells, insect cells, mammalian cells or bacteria. In exemplary embodiments of the invention, the VLPs are produced in yeast cells such as a yeast selected from the group consisting of: *Saccharomyces cerevisiae, Hansenula polymorpha, Pichia pastoris, Kluyvermyces fragilis, Kluyveromyces lactis,* and *Schizosaccharomyces pombe*. Expression of HPV VLPs in yeast cells offers the advantages of being cost-effective and easily adapted to large-scale growth in fermenters.

The present invention also includes pharmaceutical compositions comprising mutant forms of HPV VLPs, such as HPV VLPs that comprise biologically active fragments and/or mutants of an HPV L1 or L2 protein, including but not necessarily limited to amino acid substitutions, deletions, additions, amino terminal truncations and carboxy-terminal truncations such that these mutations provide for proteins or protein fragments of therapeutic or prophylactic use and would be useful for HPV VLP vaccine development. Any such mutant form of an HPV L1 protein should be capable of forming VLPs and of provoking an immune response against the desired HPV type when administered to a human.

Additionally, one of skill in the art will recognize that the L1 or L1+L2 protein, which is used to self-assemble VLPs for inclusion in the compositions disclosed herein, may be encoded by a full-length wild-type HPV L1 or L2 polynucleotide, or may be encoded by a fragment or mutant of the known wild-type sequence. Wild-type polynucleotide sequences that encode mRNA expressing HPV L1 or L2 protein are available in the art. Any mutant polynucleotide will encode either a protein or protein fragment which at least substantially mimics the pharmacological properties of an HPV L1 or L2 protein, including the ability to form VLPs that are able to provoke an immune response against the HPV type of interest when administered to a human. Any such polynucleotide includes but is not necessarily limited to: nucleotide substitutions, deletions, additions, amino-terminal truncations and carboxy-terminal truncations.

The amount of virus-like particles of each HPV type to be included in the formulations and compositions of the present invention will depend on the immunogenicity of the expressed gene product. In general, an immunologically or prophylactically effective dose comprises about 10 μg to about 100 μg, and preferably about 20 μg to 80 μg of VLPs.

Aluminum has long been shown to stimulate the immune response against co-administered antigens, primarily by stimulating a $T_H2$ response. In addition to HPV VLPs and an ISCOM-type adjuvant, the formulations of this aspect of the present invention are adsorbed to aluminum adjuvant. It is preferred that the aluminum adjuvant of the compositions provided herein is not in the form of an aluminum precipitate. Aluminum-precipitated vaccines may increase the immune response to a target antigen, but have been shown to be highly heterogeneous preparations and have had inconsistent results (see Lindblad E. B. *Immunology and Cell Biology* 82: 497-505 (2004)). Aluminum-adsorbed vaccines, in contrast, can be preformed in a standardized manner, which is an essential characteristic of vaccine preparations for administration into humans. Moreover, it is thought that physical adsorption of a desired antigen onto the aluminum adjuvant has an important role in adjuvant function, perhaps in part by allowing a slower clearing from the injection site or by allowing a more efficient uptake of antigen by antigen presenting cells.

The aluminum adjuvant of the present invention may be in the form of aluminum hydroxide ($Al(OH)_3$), aluminum phosphate ($AlPO_4$), aluminum hydroxyphosphate, amorphous aluminum hydroxyphosphate sulfate (AAHS) or so-called "alum" ($KAl(SO_4).12H_2O$) (see Klein et al., Analysis of aluminum hydroxyphosphate vaccine adjuvants by (27)Al MAS NMR., *J. Pharm. Sci.* 89(3): 311-21 (2000)). In exemplary embodiments of the invention provided herein, the aluminum adjuvant is aluminum hydroxyphosphate or AAHS. The ratio of phosphate to aluminum in the aluminum adjuvant can range from 0 to 1.3. In preferred embodiments of this aspect of the invention, the phosphate to aluminum ratio is within the range of 0.1 to 0.70. In particularly preferred embodiments, the phosphate to aluminum ratio is within the range of 0.2 to 0.50.

In some embodiments of the invention, the aluminum adjuvant is in the form of AAHS (referred to interchangeably herein as Merck aluminum adjuvant (MAA)). MAA carries zero charge at neutral pH, while AlOH carries a net positive charge and $AlPO_4$ typically carries a net negative charge at neutral pH. MAA has a higher capacity to bind HPV VLPs than AlOH. In addition, VLPs adsorbed to MAA can induce a greater humoral immune response in mice than VLPs adsorbed to AlOH. Caulfield et al., *Human Vaccines* 3: 139-146 (2007). While not wishing to be bound by theory, it is possible that net charge of the aluminum adjuvant can affect its ability to bind the VLP antigen, with strongly charged adjuvants unable to bind antigen as strongly as neutral charged adjuvants. For this reason, it is preferred that the aluminum adjuvant of the pharmaceutical compositions of the present invention have zero point surface charge at neutral pH. One of skill in the art will be able to vary the buffer, salt concentration and/or percent of free phosphate in order to allow a zero point surface charge at neutral pH.

One of skill in the art will be able to determine an optimal dosage of aluminum adjuvant that is both safe and effective at increasing the immune response to the targeted HPV type(s). For a discussion of the safety profile of aluminum, as well as amounts of aluminum included in FDA-licensed vaccines, see Baylor et al., *Vaccine* 20: S18-S23 (2002). Generally, an effective and safe dose of aluminum adjuvant varies from 150 to 600 µg/dose (300 to 1200 µg/mL concentration). In specific embodiments of the formulations and compositions of the present invention, there is between 200 and 300 µg aluminum adjuvant per dose of vaccine. In alternative embodiments of the formulations and compositions of the present invention, there is between 300 and 500 µg aluminum adjuvant per dose of vaccine.

As stated above, one aspect of the present invention provides vaccines and formulations which comprise HPV VLPs in combination with an aluminum adjuvant and an ISCOM-type adjuvant. In the formulations and methods provided herein, the ISCOM-type adjuvant comprises a saponin, cholesterol, and a phospholipid, and forms an immune-stimulating complex or ISCOM. The potent adjuvant activity of saponins, which are typically isolated from the bark of the *Quillaia saponaria* tree, was first documented over 80 years ago (for review, see Barr and Mitchell, *Immunology and Cell Biology* 74: 8-25 (1996); and Skene and Sutton, *Methods* 40: 53-59 (2006)). Compared to aluminum adjuvants, ISCOM-type adjuvants or ISCOMs are able to provoke a broader immune response to a co-administered antigen, comprising both T-cell and antibody responses. However, a potential for toxicity and haemolytic activity was found, limiting the promise of saponins for human or animal use at that time.

Since then, it was discovered that saponins, when combined with cholesterol and phospholipid, form a characteristic particle having a caged-like structure comprised of twenty or more subunits. This unique structure contributes to the adjuvant activity of the ISCOMs. Additionally, the incorporation of saponins into ISCOMs, together with cholesterol and phospholipid, was shown to eliminate the haemolytic activity of saponins. It was also shown that less adjuvant was needed to induce an immune response when ISCOMs were utilized as adjuvant compared to free saponins (see Skene and Sutton, supra). For these reasons, ISCOMs have been intensely studied as potential vaccine adjuvants.

In accordance with the present invention, it has been found that the combination of an aluminum adjuvant and an ISCOM-type adjuvant in a VLP-based vaccine can provoke stronger antibody titers than the same vaccine formulated with aluminum adjuvant alone. Additionally, it was found that HPV VLP vaccine formulations comprising both aluminum and IMX are more stable than VLP vaccines formulated without aluminum adjuvant, either in the presence or absence of ISCOMATRIX®.

To this end, the present invention relates to pharmaceutical compositions comprising VLPs of at least one type of HPV, an aluminum adjuvant, an ISCOM-type adjuvant, and a pharmaceutically acceptable carrier, said ISCOM-type adjuvant comprising a saponin, cholesterol, and a phospholipid, wherein said VLPs are comprised of recombinant L1 protein or recombinant L1+L2 proteins of HPV and wherein said VLPs are adsorbed to said aluminum adjuvant.

In specific embodiments of this aspect of the invention the VLPs of at least one type of HPV include an HPV type selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82. However, any HPV type that is associated with a pathological condition or disorder is suitable for inclusion in the pharmaceutical compositions provided herein. In some embodiments of the invention, the pharmaceutical compositions include VLPs of HPV types 6, 11, 16, and 18. In alternative embodiments, the compositions comprise VLPs of HPV types 6, 11, 16, 18, 31, 45, 52, and 58. In further embodiments, the compositions comprise VLPs of HPV types 6, 11, 16, 18, 31, 35, 45, and 58. In still further embodiments, the compositions of the invention, including the quadrivalent and octavalent compositions described, supra, further comprise VLPs of at least one additional HPV type, wherein the at least one additional HPV type is selected from the group consisting of: HPV26, HPV33, HPV35, HPV39, HPV51, HPV53, HPV55, HPV56, HPV59, HPV66, HPV68, HPV73, and HPV82.

The pharmaceutical compositions of this aspect of the present invention comprise an aluminum adjuvant, which effectively enhances the humoral immune response to an HPV type of interest, when VLPs are adsorbed to the aluminum adjuvant and administered to a patient. In specific embodiments of the invention, the aluminum adjuvant is aluminum hydroxyphosphate (AH) or amorphous aluminum hydroxyphosphate sulfate (AAHS). It is preferred that, in these specific embodiments, the aluminum adjuvant comprises phosphate and aluminum present in a molar ratio of about 0.1 to about 1.1 phosphate ($PO_4$) to aluminum (Al). It is more preferred that the aluminum adjuvant comprises phosphate and aluminum present in a molar ratio of about 0.2 to about 0.5 PO$_4$/μM. In alternative embodiments of this aspect of the invention, the aluminum adjuvant is aluminum hydroxide.

The ISCOM-type adjuvant of the compositions provided herein may be prepared by any one of several known methods for producing ISCOMs known in the art (for review, see Barr and Mitchell, *Immunology and Cell Biology* 74: 8-25 (1996)). Well-known methods of production include a centrifugation method and a dialysis method, as described in Barr, supra. ISCOM adjuvants may also be obtained from a commercial source. ISCOM-type vaccines are formulated with *Quillaja saponins*, cholesterol, and phospholipids such as phosphphatidylcholine, although it has been found that almost any phospholipid is useful in the formation of an ISCOM particle (see Barr and Mitchell, supra).

In preferred embodiments of the present invention, the ISCOM-type adjuvant is a so-called ISCOM-matrix adjuvant, such as ISCOMATRIX® (CSL Ltd., Parkville, Australia), which comprises the ISCOPREP® saponin (CSL Ltd., Parkville, Australia) cholesterol, and dipalmitoylphosphatidylcholine.

The compositions of the present invention optimally comprise between 10 and 200 μg of ISCOM-matrix adjuvant per 0.5 mL dose of VLP vaccine (20-400 μg/mL). In exemplary embodiments of this aspect of the invention, the ISCOM-type adjuvant is ISCOMATRIX®.

The present invention also relates to HPV vaccine formulations comprising: A human papillomavirus (HPV) vaccine formulation comprising: (a) HPV virus-like particles (VLPs) of at least one HPV type, wherein the HPV type is selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; said HPV VLPs comprised of recombinant L1 or recombinant L1+L2 protein of HPV; wherein the VLPs of any one HPV type are present in a concentration of about 10 μg to about 100 μg and wherein the total VLP concentration is between 10 μg and 600 μg; (b) from about 150 μg to about 600 μg of aluminum adjuvant; and (c) from about 10 μg to about 200 μg of an ISCOM-type adjuvant; wherein said HPV VLPs are adsorbed onto said aluminum adjuvant In specific embodiments of this aspect of the invention, the HPV vaccine formulations comprise (a) from about 20 μg to about 80 μg of VLPs of at least one HPV type; (b) from about 200 μg to about 300 μg of the aluminum adjuvant; and (c) from about 15 μg to about 120 μg of the ISCOM-type adjuvant. In other embodiment, the formulation further comprises from about 20 μg to about 60 μg of VLPs of at least one additional HPV type.

The instant invention relates, in one embodiment, to HPV vaccine formulations comprising VLPs of HPV types 6, 11, 16, and 18. The present invention also provides HPV vaccine formulations, further comprising VLPs of HPV types 31, 45, 52, and 58. The present invention further provides HPV vaccine formulations, as described above, further comprising HPV types 31, 35, 45, and 58.

In certain aspects of the invention provided herein, there is provided HPV vaccine formulations comprising an ISCOM-type adjuvant, wherein the ISCOM-type adjuvant is ISCOMATRIX®.

Also provided herein is an HPV vaccine formulation comprising: (a) from about 20 μg to about 40 μg of VLPs of each of HPV types 6, 11, 16, 18, 31, 45, 52, and 58, said HPV VLPs comprised of recombinant L1 or recombinant L1+L2 protein of HPV; (b) from about 200 μg to about 300 μg of aluminum adjuvant; and (c) from about 30 μg to about 120 μg of an ISCOM-type adjuvant, said ISCOM-type adjuvant comprising a saponin, cholesterol, and a phospholipid; wherein said HPV VLPs are adsorbed onto said aluminum adjuvant.

The HPV types to be used in the vaccine formulation above may be substituted with other HPV types, or combination thereof, such as an octavalent vaccine formulation comprising HPV types 6, 11, 16, 18, 31, 35, 45, and 58.

The pharmaceutical compositions and formulations of the current invention may be used to induce a durable and efficacious immune response to HPV in a patient, and to prevent HPV infection. To that end, the present invention provides a method of inducing an immune response to HPV in a human patient comprising administering to the patient a pharmaceutical composition comprising HPV VLPs, an aluminum adjuvant, and an ISCOM-type adjuvant, said ISCOM-type adjuvant comprising a saponin, cholesterol, and a phospholipid; wherein said HPV VLPs are comprised of recombinant L1 protein or recombinant L1+L2 protein of HPV and wherein said VLPs are adsorbed to the aluminum adjuvant.

The present invention also provides a method of preventing infection of a human patient by a HPV comprising administration of a pharmaceutical composition comprising recombinant HPV VLPs, aluminum adjuvant, and an ISCOM-type adjuvant to the patient, wherein said ISCOM-type adjuvant comprises a saponin, a sterol, and a phospholipid, wherein the HPV VLPs are comprised of recombinant L1 protein or recombinant L1+L2 protein of HPV and wherein said VLPs are adsorbed to the aluminum adjuvant.

In specific embodiments of the methods provided herein, the pharmaceutical composition that is administered to the patient comprises VLPs of HPV types 6, 11, 16, and 18. In additional embodiments, the compositions further comprise VLPs of HPV types 31, 45, 52, and 58. In further embodiments, the compositions further comprise VLPs of HPV types 31, 35, 45, and 58. In other embodiments, the compositions further comprise VLPs of at least one additional HPV type selected from the group consisting of: HPV26, HPV33, HPV35, HPV39, HPV51, HPV53, HPV55, HPV56, HPV59, HPV66, HPV68, HPV73, and HPV82.

Vaccine compositions of the present invention may be used alone at appropriate dosages which allow for optimal inhibition of HPV infection with minimal potential toxicity. In addition, co-administration or sequential administration of other agents may be desirable.

The formulations and compositions of the present invention may be administered to a patient by intramuscular injection, subcutaneous injection, intradermal introduction, or impression though the skin. Other modes of administration such as intraperitoneal, intravenous, or inhalation delivery are also contemplated. In preferred embodiments of the invention, the vaccines and pharmaceutical compositions are administered by intramuscular administration.

In some embodiments of this invention, the HPV pharmaceutical compositions and formulations disclosed herein are administered to a patient in various prime/boost combinations in order to induce an enhanced, durable, immune response. In this case, two pharmaceutical compositions are administered in a "prime and boost" regimen. For example the first composition is administered one or more times, then after a predetermined amount of time, for example, 2 weeks, 1 month, 2 months, six months, or other appropriate interval, a second composition is administered one or more times.

Preferably, the two or more HPV pharmaceutical compositions used in a clinical regimen comprise VLPs of the same HPV type or combination of HPV types. However, it may also be desirable to follow a clinical regimen in which two different HPV pharmaceutical compositions are administered to a patient with an appropriate interval of time separating the two vaccine administrations. For example, a vaccine composition comprising HPV16 and 18 VLPs may be administered at one point in time, followed by an HPV vaccine composition comprising HPV 31, 45, 52, and 58 VLPs at a second point in time, after a pre-determined length of time has passed. In such cases, each of the two different HPV vaccine compositions may be administered to the patient once, or more than one time, separated by an appropriate length of time.

In accordance with one aspect of the present invention, it was shown that that a two-dose clinical regimen using an HPV VLP vaccine adjuvanted with both AAHS and ISCO-MATRIX® can induce an immune response of comparable magnitude as a three-dose regimen using VLP vaccine adjuvanted with AAHS alone (see EXAMPLE 1).

In that respect, the present invention provides a method of preventing HPV infection in a human patient comprising: (a) introducing into the patient a first pharmaceutical composition comprising recombinant HPV VLPs, aluminum adjuvant, and an ISCOM-type adjuvant to the patient, wherein said ISCOM-type adjuvant comprises a saponin, a sterol, and a phospholipid, wherein the HPV VLPs are comprised of recombinant L1 protein or recombinant L1+L2 protein of HPV and wherein said VLPs are adsorbed to the aluminum adjuvant; (b) allowing a predetermined amount of time to pass; and (c) introducing into the patient a second pharmaceutical composition comprising recombinant HPV VLPs, aluminum adjuvant, and an ISCOM-type adjuvant to the patient, wherein said ISCOM-type adjuvant comprises a saponin, a sterol, and a phospholipid, wherein the HPV VLPs are comprised of recombinant L1 protein or recombinant L1+L2 protein of HPV and wherein said VLPs are adsorbed to the aluminum adjuvant.

In specific embodiments of the method described above, the first and second compositions are the same and the clinical regimen includes at least one injection of the composition to "prime" the immune response to HPV and at least one injection to "boost" the immune response. However, other methods in which multiple injections to prime and/or boost the immune response are also contemplated by the invention described herein.

In some circumstances, it may be desirable to provide a multi-dose HPV vaccine formulation which comprises more than one dose of vaccine in the same vial. If a multi-dose formulation is desired, an anti-microbial preservative should be used to kill or prevent the growth of microorganisms, such as bacteria and fungi. Multi-dose vaccine formulations containing anti-microbial preservatives provide several advantages over single dose formulations, including allowing multiple doses of vaccine to be withdrawn from the vial over a period of time without the concern that the first withdrawal inadvertently introduced microbial contamination (Meyer et al., *J. Pharm. Sci.* 96(12): 3155-3167 (2007)). Many marketed vaccine products, which are unrelated to HPV, comprise phenoxyethanol (DAPTACEL® (Sanofi Pasteur, Lyon, France), PEDIARIX®, INFANRIX®, HAVRIX®, and TWINRIX® (GlaxoSmithKline (GSK), Brentford, Middlesex, United Kingdom) or thimerosal (PEDIARIX® and ENGERIX-B® (GSK)) as anti-microbial preservatives (see Meyer et al., supra). In addition PNEUMOVAX® 23 (Merck & Co., Inc., Whitehouse Station, N.J.) formulations contain phenol as an antimicrobial preservative. However, the compatibility of HPV VLP-containing vaccine formulations with anti-microbial preservatives has not been previously addressed.

Thus, in accordance with one aspect of the present invention, it was shown that the addition of an antimicrobial preservative selected from the group consisting of: m-cresol, phenol, and benzyl alcohol, to vaccine formulations comprising HPV VLPs is effective at reducing or eliminating microbes and does not negatively impact the structural and thermal stability of the VLPs at 2-8° C. It is also shown herein that anti-microbial preservatives selected from the group consisting of: m-cresol, phenol, and benzyl alcohol are an effective preservative in HPV vaccine formulations comprising HPV VLPs in combination with an ISCOM-type adjuvant. Thus, the invention also relates to HPV vaccine formulations comprising HPV VLPs and an antimicrobial preservative selected from the group consisting of: m-cresol, phenol and benzyl alcohol. The vaccine formulations according to this aspect of the invention may also include and ISCOM-type adjuvant and an aluminum adjuvant, as described above.

In some preferred embodiments of this aspect of the invention, m-cresol is included in the multi-dose HPV vaccine formulation at a concentration of about 0.15 to about 0.31%. In more preferred embodiments, the multi-dose vaccine formulations comprise m-cresol at a concentration of about 0.25 to about 0.31%. In one preferred embodiment, m-cresol is included in the multi-dose formulation at a concentration of about 0.3%.

In alternative embodiments of the invention, phenol is included in the multi-dose HPV VLP vaccine formulations at a concentration of about 0.25 to about 0.55%. In more preferred embodiments, phenol is included at a concentration of about 0.4 to about 0.55%. In one particularly preferred embodiment, a multi-dose HPV VLP vaccine formulation comprising phenol at a concentration of about 0.5% is provided.

In still further embodiments, the multi-dose HPV vaccine formulations comprise benzyl alcohol at a concentration of about 0.75 to about 1.2%. In more preferred embodiments, benzyl alcohol is included in the multi-dose vaccine formulation at a concentration from about 0.8% to about 1.0%. In a particularly preferred embodiment of this aspect of the invention, the concentration of benzyl alcohol is 0.9%.

Accordingly, one aspect of the present invention relates to a multi-dose HPV vaccine formulation comprising: (a) HPV virus-like particles (VLPs) of at least one HPV type, wherein the HPV type is selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; said HPV VLPs comprised of recombinant L1 or recombinant L1+L2 protein of HPV; (b) an aluminum adjuvant; and (c) an anti-microbial preservative selected from the group consisting of: m-cresol, phenol and benzyl alcohol; wherein said HPV VLPs are adsorbed onto said aluminum adjuvant.

The multi-dose HPV vaccine formulation described above may optionally include an ISCOM-type adjuvant.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

Development of HPV Formulations Comprising Adjuvants:

EXAMPLE 1

Administration of HPV Octavalent Vaccine with Iscomatrix Adjuvant to Rhesus Macaques To determine if the immune response against HPV VLP-based vaccine could be increased beyond titers achieved with an aluminum adjuvant alone, an octavalent HPV VLP vaccine was administered to rhesus macaques in combination with amorphous aluminum hydroxyphosphate sulfate (AAHS) plus the ISCOMATRIX® adjuvant.

The vaccine consisted of eight different HPV L1 virus-like particles. The VLPs were adsorbed onto aluminum hydroxide phosphate adjuvant (MAA) present at 450 mcg/mL concentration. The MAA-adsorbed vaccines were tested either with or without further addition of ISCOMATRIX® (CSL Limited ABN, Parkville, Australia) present at 200 mcg/mL. The vaccines were in buffer that consisted of 0.32 M NaCl, 10 mM Histidine (pH 6.2) and 0.01% polysorbate-80. A single injection of 0.5-mL volume of the vaccine was given to the right deltoid of each Indian rhesus macaque.

TABLE 1

Concentrations of each VLP type in the vaccine and amounts given to each animal.

|  | HPV6 | HPV11 | HPV16 | HPV18 | HPV31 | HPV45 | HPV52 | HPV58 |
| --- | --- | --- | --- | --- | --- | --- | --- | --- |
| mcg/ml | 4 | 8 | 8 | 4 | 4 | 4 | 4 | 4 |
| Dose (0.5 ml) | 2 | 4 | 4 | 2 | 2 | 2 | 2 | 2 |

The following immunization schedules were tested (n=4 for each group): Group I received immunizations with the MAA-adjuvanted octavalent vaccine at weeks 0 and 8; Group II received immunizations with the MAA/IMX-adjuvanted vaccine at weeks 0 and 8; Group III received immunizations with the MAA/IMX-adjuvanted vaccine at weeks 0, 8, and 24; and Group IV received immunizations with the MAA/IMX-adjuvanted vaccine at weeks 0 and 24. Serum samples were collected from each animal at 4 weeks interval.

Results indicate that all animals that were immunized with either the MAA-adjuvanted or the MAA/IMX-adjuvanted vaccine seroconverted to each of the eight HPV types. When comparing Groups I and II, the geometric mean titers against each of the HPV types were consistently elevated in the MAA/IMX-adjuvanted vaccine recipients (Group II) compared to the MAA-adjuvanted vaccine recipients (Group I). The improvement remained apparent at week 52, suggesting that the effect is long-lived.

Figure 2:
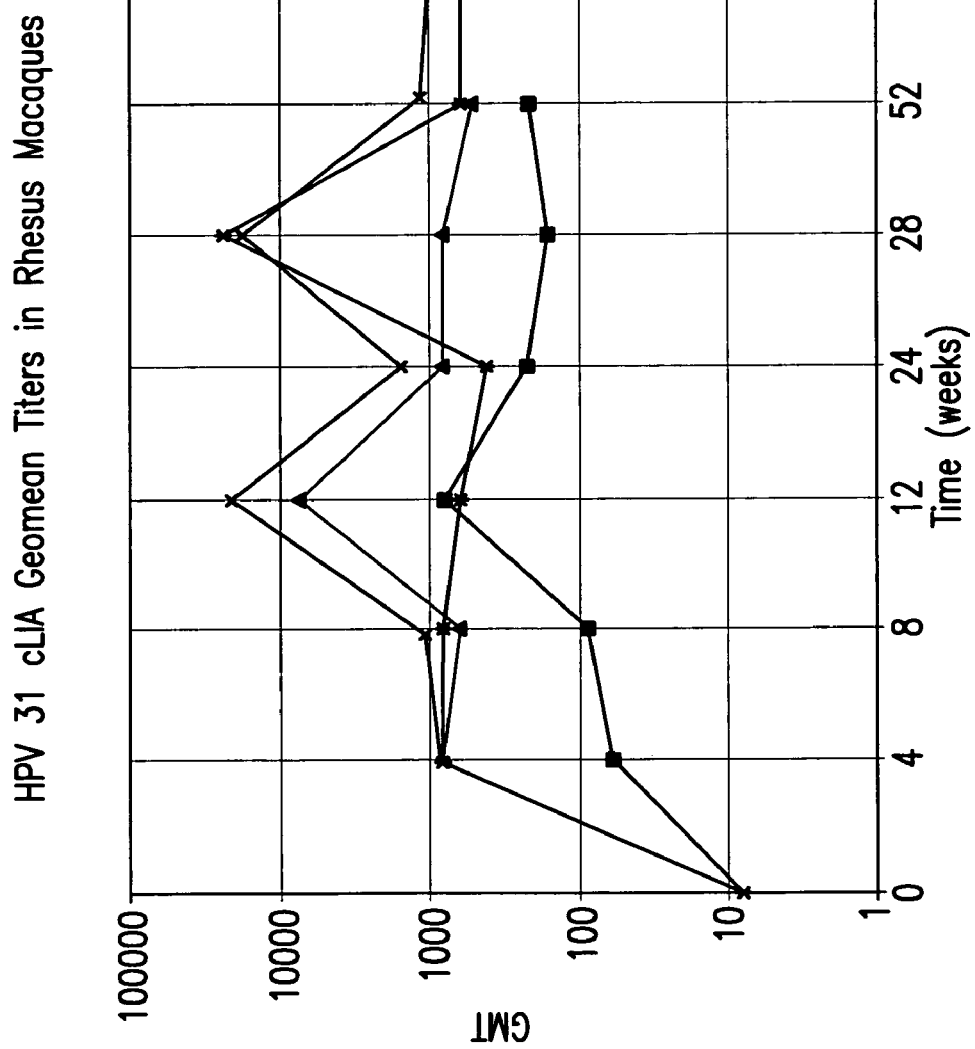
FIG. 2 shows the anti-HPV 31 geometric mean titers (GMT) by vaccination group among rhesus macaques immunized with an experimental octavalent HPV VLP vaccine over time. The vaccines were adjuvanted either with MAA or MAA+IMX, according to the indicated immunization schedule and as described in EXAMPLE 1.

When comparing Groups I and IV, results show that after a single dose, the peak titers of the MAA/IMX-adjuvanted vaccine cohort (Group IV) were not only higher than that elicited by a single dose of MAA vaccine (Group I), but also were comparable to the peak titers elicited by two doses of the MAA vaccine (for representative results for HPV16 and 31, see FIGS. 1 and 2) The titers at week 52 for the 0, 24 dosing regimen with MAA-1-adjuvanted vaccine (Group IV) were only slightly lower than those for the 0, 8, 24-dosing regimen with the same vaccine (Group III). This suggests that a two-dosing regimen using the MAA/IMX-adjuvanted vaccine has the potential of inducing comparable levels of immune response as a 3 dosing-regimen with MAA-adjuvanted vaccine.

EXAMPLE 2

HPV Competitive Luminex Assay

To demonstrate an immune response, sera extract from immunized monkeys were analyzed by competitive Luminex immunoassay (cLIA). The HPV cLIA utilizes eight type-specific, conformational dependent mAbs to monitor the immune response to immunization with an HPV Octavalent vaccine. A more detailed description of the competitive Luminex immunoassay, which utilizes particle-based flow cytometric analysis to simultaneously measure the presence of antibodies to a plurality of HPV types in a test sample, is set forth in U.S. Pat. No. 7,067,258, and in Opalka et al. *Clin Diagn Lab Immunol.* 10(1): 108-15 (2003). An octavalent reference standard solution was prepared for each HPV type in a pre-screened assay matrix containing Antibody Depleted Human Serum (ADHS). The reference standard was a pool of serum samples from Rhesus macaques hyper-immunized with HPV monovalent L1 VLP types 6, 11, 16, 18, 31, 45, 52, 58. All standards, controls and samples were tested in dupli-cate. Testing of serum samples were performed at a 1:4, 1:40, 1:400, or 1:4000 dilution. Fluorescent units were read and duplicate wells averaged. Dilution corrected mMU/mL serum values were computed based on four parameter logistics fit of the standard curve on each assay plate. Samples that exceeded the limits of quantitation for the standard curve were re-tested at higher dilutions. Duplicates that failed extra variability were not reported and the samples were then retested until they passed the duplicate parameters. Control specifications for the assay were developed and limits of quantitation were established for each HPV type.

EXAMPLE 3

Immunogenicity of HPV VLP Vaccines in Combination with MAA and Iscomatrix® Adjuvants The ability of ISCOMATRIX® (IMX) to enhance the immune response to HPV in human patients was evaluated in clinical trials. A two phase, randomized, double-blind, multicenter, IMX dose-escalation controlled study was initiated which tested an octavalent HPV VLP vaccine adjuvanted with amorphous aluminum hydroxyphosphate sulfate (MAA). Subjects were randomized in two separate study phases. IMX concentrations of 15 or 30 mcg (Phase A) and 60 or 120 mcg (Phase B) per each 0.5-mL dose were evaluated in the context of an experimental octavalent vaccine containing a fixed concentration of HPV VLPs formulated with MAA (281 mcg) and compared to GARDASIL®. The octavalent vaccine contained HPV VLPs of types 6 (20 mcg), 11 (40 mcg), 16 (40 mcg), 18 (20 mcg), 31 (20 mcg), 45 (20 mcg), 5 (20 mcg), and 58 (20 mcg). GARDASIL® is a quadrivalent HPV (Types 6, 11, 16, 18) recombinant vaccine prepared from highly purified L1 VLPs. In addition to VLPs, each vaccine dose contained MAA (225 mcg), sodium chloride, L-histidine, polysorbate 80, sodium borate, and water.

In each arm of the study, vaccine was administered at day 1, month 2, and month 6 as a 0.5-mL intramuscular injection of either one of the four formulations of octavalent HPV L1 VLP with MAA/IMX described above, or GARDASIL®. The study included ~150 healthy women between the ages of 18 and 24 years at the time of enrollment. Blood samples taken at day 1, month 2, month 3 (1 month post-dose 2), month 6, month 7 (1 month post-dose 3), and month 12 were used for evaluation of immune response to relevant HPV types using a competitive Luminex immunoassay (cLIA), as described in EXAMPLE 2.

An analysis of immune response to the vaccine formulations relative to that of GARDASIL® was conducted in which 145 subjects in Phase A and Phase B (97%) had month 3 (Postdose 2) immunogenicity data available and 73 subjects in Phase A (97%) also had month 7 (Postdose 3) immunogenicity data available. The analysis included subjects in Phase A if they: (i) received all 3 vaccinations in the appropriate day ranges, (ii) had serology samples collected in appropriate day ranges, (iii) were seronegative to the relevant HPV types at Day 1, and (iv) had a valid month 7 serology result collected in the appropriate day range. Subjects in Phase B were included in the analysis if they: (i) received the first 2 vaccinations in the appropriate day ranges, (ii) had serology samples collected in appropriate day ranges, and (iii) were seronegative to the relevant HPV types at Day 1.

Results at both the month 3 (postdose 2) and month 7 (postdose 3) time-points by treatment group for subjects in Phase A (15 and 30 mcg IMX, +MAA) and at the month 3 time-point for subjects in Phase B (60 and 120 mcg IMX, +MAA) are displayed in FIGS. 3 and 4, respectively. The results demonstrate an IMX dose-related enhancement of the immune response to relevant HPV types compared to that of GARDASIL®, which is adjuvanted with MAA alone.

EXAMPLE 4

Stability of Octavalent HPV MAA and Solution Formulations in the Presence and Absence of ISCOMATRIX® (IMX)

Four different octavalent HPV samples, ±MAA and ±IMX, were formulated. All formulations contained HPV VLPs in the following amounts: 40 µg/mL HPV 6, 80 µg/mL HPV11, 80 µg/mL HPV16, and 40 µg/mL each of HPV18, 31, 45, 52, and 58 VLPs. Also included in each of the formulations was 0.32 M NaCl, 10 mM Histidine pH 6.2 and 0.01% polysorbate 80 (PS80). The first formulation contained no IMX or MAA adjuvant. The second formulation contained 240 µg/mL IMX and no MAA. The third formulation that was tested contained no IMX and 562.5 µg/mL (1.25×) MAA. The fourth formulation that was tested contained both 240 µg/mL IMX and 562.5 µg/mL (1.25×) MAA.

These four formulations were analyzed by SDS-PAGE for HPV VLP integrity and in vitro relative potency assay (IVRP) for in-vitro antigenicity after being stored for 6 months at 4° C. and 37° C. Results from SDS-PAGE analyses (EXAMPLE 5) as well as UVRP assays (EXAMPLE 6) indicated that HPV VLPs are not stable without MAA, and IMX has no impact on HPV VLP stability in the presence of MAA. Results demonstrate that MAA should be included in IMX-containing HPV vaccine formulations.

EXAMPLE 5

Evaluation of HPV VLP Integrity by SDS-PAGE

Samples were analyzed by SDS-PAGE with Invitrogen 4-20% or 14%, 1.5 mm, 10 well Tris-Glycine gels. Samples are prepared in a reducing sample buffer (0.25M Tris PH 6.8, 8% SDS, 40% Glycerol, 0.008% Bromophenol blue, dithiothreitol, and heated at 70° C. for 10 minutes). The samples containing aluminum adjuvant were concentrated to 762 µg/mL prior to sample preparation, and 0.5M EDTA, pH 8.0 was included to dissolve the aluminum.

The high load was added to a 1× reducing sample buffer (portions of one 4× reducing sample buffer: three MilliQ water) to prepare a low load (2.5 µg). A 12 mcg (high) and a 2.5 mcg (low) load were run for each sample.

After electrophoresis, gels were fixed using a 12% (w/v) trichloroacetic acid solution and stained with a Pro-Blue Colloidal Coomassie Blue Stain. Band patterns were acquired using a densitometer and analyzed using ImageQuant software (GE Healthcare Biosciences; Piscataway, N.J. The high load was used to determine the relative amounts of degradants and the low load was used to determine the relative amount of intact HPV.

Figure 5:
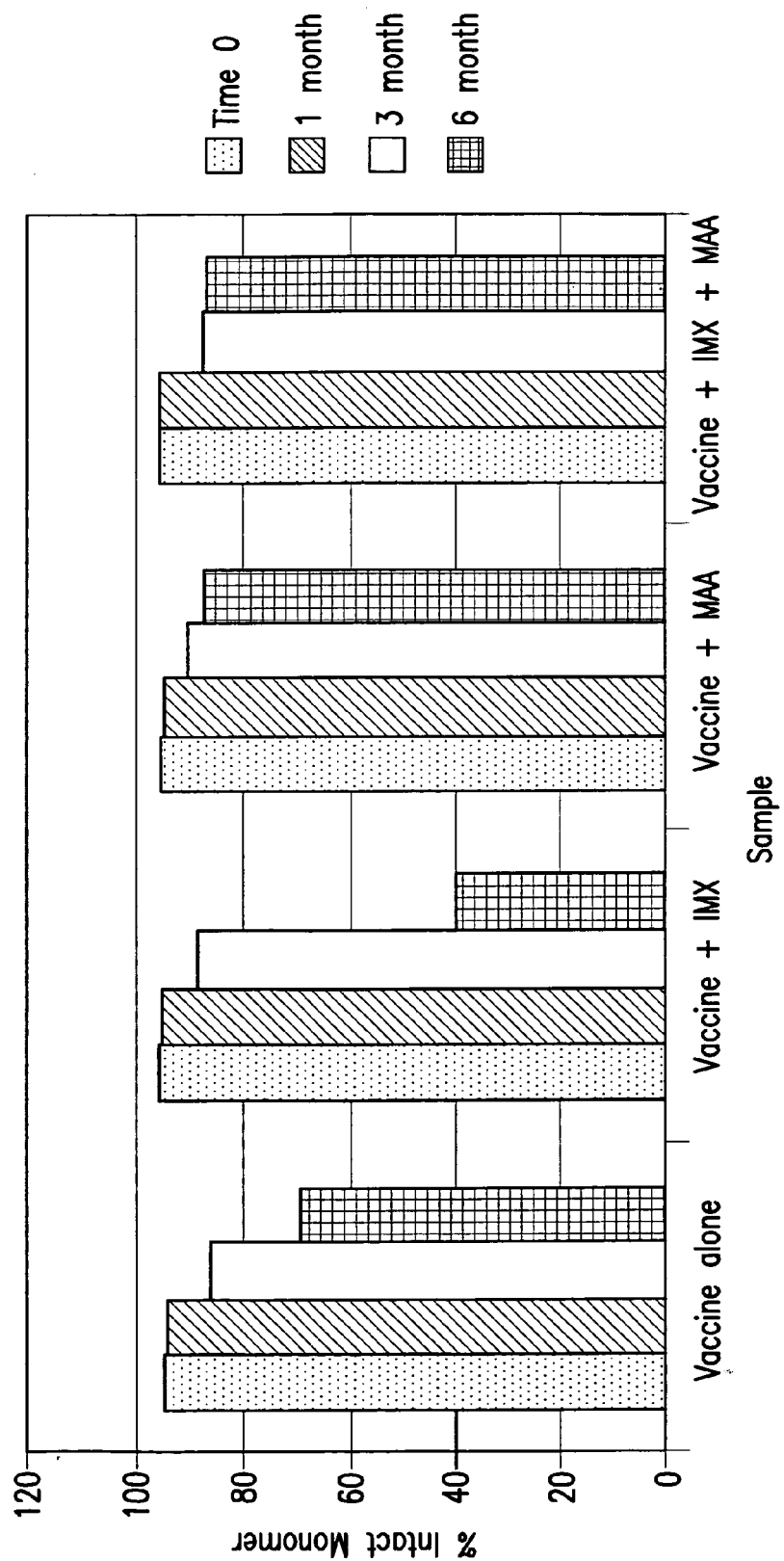
FIG. 5 shows the percent of intact monomer of octavalent HPV VLP vaccine samples stored at 37° C. over time. Shown are results from SDS-PAGE analysis of octavalent vaccine formulations ±ISCOMATRIX and ±MAA adjuvant (see EXAMPLES 4 and 5). Data are provided at Time=0 (dotted bars), 1 month (striped bars), 3 months (solid bars) and 6 months (hatched bars).

Results indicated that there was a small decrease (less than 10%) in % intact monomer for both of the plus-MAA samples (±IMX) stored at 37° C. after 6 months (FIG. 5). However, there were much larger decreases in % intact monomer for both of the minus-MAA samples at the same time point and storage, to 69% for the minus-IMX sample and to 39% for the plus-IMX sample. The data demonstrate that in the presence of IMX, HPV VLPs are more stable in MAA formulation than in solution formulation.

EXAMPLE 6

Evaluation of In Vitro Antigenicity of HPV VLPs by IVRP Assay

The potencies of HPV types 6, 11, 16, 18, 31, 45, and 52 VLP samples were quantified relative to a reference standard by in vitro relative potency (IVRP) testing. The IVRP assay is a sandwich-type immunoassay that uses separate monoclonal antibodies for capture and detection.

The antibodies used in each of the eight serotype-specific assays were prepared by Strategic BioSolutions (Newark, Del.). The following serotype-specific capture antibodies were used in the IVRP assay: H6.M48 mAb ($IgG_1$) for HPV6, K11.B2 mAb ($IgG_1$) for HPV11, H16.J4 mAb ($IgG_{2a}$) for HPV16, H18.J4 mAb ($IgG_{2a}$) for HPV18, H31.5F12.D4 mAb ($IgG_1$) for HPV31, H45.6G6.A8 mAb ($IgG_{2b}$) for HPV45, H52.8D11.C4 mAb ($IgG_{2b}$) for HPV52, and H58.2; C3.F7 mAb ($IgG_1$) for HPV 58. The following serotype-specific detection antibodies were used in the assay: H6.B10.5 mAb ($IgG_{2b}$) for HPV6, H11.B2 mAb ($IgG_{2b}$) for HPV11, H16.V5 mAb ($IgG_{2b}$) for HPV16, H18.R5 mAb ($IgG_{2b}$) for HPV18, M31.5D10.E4 mAb ($IgG_{2b}$) for HPV31, H45.10B4.H4 mAb ($IgG_1$) for HPV45, H52.9F7.E10 mAb ($IgG_{2a}$) for HPV52, and H58.6E11.F4 mAb ($IgG_{2b}$) for HPV58.

The assay was carried out on a Tecan Freedom EVO workstation (Tecan USA; Research Triangle, NC) using white FluoroNunc MaxiSorp 96-well microtiter plates (Fisher Scientific; Pittsburgh, Pa.). Assay plates were first coated with the capture antibody (100 µL/well), in 1 M ammonium sulfate buffered with 10 mM Tris, pH 8, and then allowed to incubate for 16-24 hrs at 2-8° C. Following the incubation, the plates were washed with Tris-buffered Saline (TBS) containing 0.05% Tween 20 and then blocked with 200 µL/well of assay diluent (TBS containing 0.05% Tween 20 and 1% bovine serum albumin) for one hour. Prior to sample addition, adjuvant-adsorbed samples and standards were diluted 5-fold in 6% citrate phosphate buffer (pH 6.7-6.8) containing 1 M NaCl and 0.04% Tween 80 and incubated for 2±0.5 hrs at ambient temperature on a nutator for adjuvant dissolution. Samples that were not adsorbed to adjuvant were also diluted in the dissolution buffer but were not incubated. Each sample and reference standard was then diluted to a serotype-specific target concentration with assay diluent in a Nunc 96-well polypropylene microtiter plate from Fisher Scientific (Pittsburgh, Pa.). From this initial dilution, eleven two-fold serial dilutions were prepared for each sample and for the reference standard in the assay plate. After a 12-20 hour incubation at room temperature with shaking, the plates were washed and 100 μL of the detection antibody was subsequently added to each well. The plate was incubated for one hour at room temperature and again washed.

Next, 100 μL of rat anti-mouse monoclonal antibody ($IgG_1$, $IgG_{2a}$, or $IgG_{2b}$) conjugated to alkaline-phosphatase was added to each well, supplied from Southern Biotechnology (Birmingham, Ala.) or BD Pharmingen (BD Biosciences; San Jose, Calif.). After a one-hour incubation at room temperature, the plate was washed to remove any unbound conjugate. Next, 100 μL of 4-methylumbelliferyl phosphate (4-MUP) substrate solution from ViroLabs (SuperPhos; Chantilly, Va.) was added and allowed to react for one hour.

The fluorescence of each well was measured by reading the plate in a Tecan Ultra Evolution 384 plate reader (Tecan USA; Research Triangle, NC) at an excitation wavelength of 360 μm and an emission wavelength of 450 nm. The resulting fluorescence intensity was plotted relative to the dilution factor and the data was analyzed using a four-parameter logistic model:

$$y = D + \frac{(A-D)}{1 + \left(\frac{X}{C}\right)^8}$$

where X is the sample dilution, y is the measured fluorescence response, A is the asymptotic maximum, B is the slope, C is the ED50 (i.e. the theoretical dilution that produces a response equal to 50% of the maximum response) and D is the asymptotic minimum. The same asymptotic maximum and minimum were applied to both the standard and the sample, and the ED50 and the slope for each sample and standard were iteratively adjusted until the root mean square error was minimized. Once the optimal ED50 and slope for each individual sample and standard were identified, a test for parallelism was applied to the sample. If the sample slope was within 20% of the reference standard slope, the test sample were considered parallel to the standard, and the data was reanalyzed using a common slope model. A common slope, asymptotic maximum and asymptotic minimum were applied to both the sample and the standard, and the sample and standard ED50's were independently optimized to minimize the root mean square error. The final IVRP was calculated using the following equation:

$IVRP = (ED_{50}sample/ED_{50}standard) \times Reference\ Standard\ Potency$

The results were subsequently normalized by dividing by the protein concentration, thus producing the IVRP-to-protein ratio. The IVRP-to-protein ratio provides a measure of the functional epitopes per unit of mass.

The results indicate that all eight types of HPV antigens retained 100% antigenicity after being stored at 4° C. for 6 months in both of the plus— and minus-MAA samples regardless of the presence and absence of IMX (see FIG. 6). The antigenicities of all HPV types in both of the minus-MAA formulations (±IMX) remained only 10% after 6-months at 37° C. However, each HPV type in both of the plus-MAA formulations (±IMX) was still above 75% active, suggesting that HPV VLPs in the absence of MAA were not stable. The IVRP results are comparable with the SDS-PAGE date, indicating that MAA is needed in the IMX-based HPV formulation.

Development of HPV Formulations Comprising Preservatives:

EXAMPLE 7

Evaluation of the Effectiveness of Anti-Microbial Preservatives

The effectiveness of various preservatives in candidate HPV vaccine formulations was evaluated using an antimicrobial test (anti-microbial effectiveness (AME) test). AME testing was used to determine the ability of a preservative to reduce or eliminate microbes that may be introduced into the vial following product withdrawal. For description of the assay, see United States Pharmacopoeia (USP)<51>, European Pharmacopoeia 5.1.3, and Meyer et al. *J. Pharm. Sci.* 96(12):3155-3167 (2007), which is herein incorporated by reference. Briefly, the AME test comprises the EPA, EPB and USP criteria, which consist of inoculating $10^5$-$10^6$ CFU/mL microorganisms (e.g., bacteria and fungi) per container at time zero, and evaluating the log reduction over time (Meyer et al., supra).

The initial preservative screening was conducted using the following seven preservatives: benzyl alcohol, chlorobutanol (plus EtOH), m-cresol, methylparaben, propylparaben, phenol, and 2-phenoxyethanol in various doses and combinations. These preservatives have been used as anti-microbial preservatives in commercial parenteral products. Thimerosal was also included as a reference.

The initial doses and combinations of the preservatives were selected based on previous work and available literature. More specifically, concentrations were tested ranging from 0.5-1.2% benzyl alcohol; 0.25-0.5% chlorobutanol (0.5% EtOH or 3.0% EtOH); 0.15-0.3% m-cresol; 0.045-0.18% methylparaben; 0.005-0.02% propylparaben; 0.25-0.5% phenol; 0.25-0.5% 2-phenoxyethanol; and 0.002-0.01% thimerosal. All samples contained 562.5 mcg/mL MAA, 0.32 M NaCl, 10 mM His, 0.01% polysorbate-80 (PS-80), pH 6.2. Formulations containing chlorobutanol and propylparaben were tested with and without the addition of 120 mcg/mL ISCOMATRIX®.

Benzyl alcohol, phenol, 2-phenoxyethanol, and m-cresol were provided as solutions and were added directly to the HPV formulations. Chlorobutanol was provided in a powder and was dissolved in 100% ethanol to make a stock solution. Thimerosal was dissolved in USP water to make a stock solution. The combination of methylparaben and propylparaben were made by weighing out each powder and making a stock solution in 100% ethanol. The pH of the solution was adjusted with a target pH of 6.2.

Preservatives were added to octavalent HPV formulations comprising 8 types of HPV VLPs, as described in EXAMPLE 1, and were stored for one week at 2-8° C. prior to AME testing. Formulations containing 1.2% benzyl alcohol, 0.5% chlorobutanol, and 0.3% m-cresol passed the USP, EP-B, and EP-A criteria of the AME test (See Meyer et al., supra). Formulations containing 0.4% and 0.5% phenol passed USP and EP-B, but not EP-A tests. Additional preservative-containing formulations were tested that only passed the USP test. Therefore, formulations containing 1.2% benzyl alcohol, 0.5% chlorobutanol, 0.3% m-cresol, and phenol at a concentration of 0.4% or 0.5% were selected for further evaluation.

EXAMPLE 8

Evaluation of the Impact of Preservatives on the Structural Stability of HPV VLP Antigens Differential Scanning Calorimetry (DSC) was used to evaluate the impact of preservatives on protein structural and thermal stability. The analysis for antigen thermal stability was determined using a VP-Capillary DSC Platform (Micro-Cal, LLC, Northampton, Mass.). A detailed description of the conditions utilized is disclosed in Ionescu et al. (2007) (*J. Pharm. Sci.* 97(4): 1414-1426 (2008)).

HPV18 VLPs were chosen as the model HPV antigen for DSC analysis because this type of VLP gives the most robust DSC signals and represents a less stable type of VLP compared to other types tested. The DSC evaluation was carried out in the presence of various preservatives with varied concentrations. The results indicate that 0.5% chlorobutanol, 0.15% m-cresol, 0.25% phenol, 0.5% ethanol (solvent for chlorobutanol), and 0.25% 2-phenoxyethanol had the least impact on the thermal stability of HPV type 18 (data not shown). The greatest impact on the thermal stability was observed with thimerosal, 1.2% benzyl alcohol, and 0.045/0.005 methylparaben. However, because the 1.2% benzyl alcohol formulation passed EP-A (EXAMPLE 7) and also had a high biacore response (EXAMPLE 9), it was still selected for further stability testing (EXAMPLEs 11-12). Also, although higher concentrations of m-cresol (0.3%) and phenol (0.5%) had a relatively greater impact on the thermal stability when compared to lower concentrations of these preservatives, the higher concentrations were selected for further evaluation due to passing EP-A (0.3% m-cresol) and EP-B (0.5% phenol) (see EXAMPLE 7). The preservative 2-phenoxyethanol was not considered for further evaluation because it did not pass EP-B or EP-A (see EXAMPLE 7).

EXAMPLE 9

Impact of Preservatives on the Activity of HPV VLP Antigens

The in vitro antigenicity of HPV vaccine formulations comprising HPV18 VLPs and different preservatives was evaluated using a neutralization antibody binding assay (Biacore, Surface Plasmon Resonance). The analysis for antigen bioactivity was determined using the Biacore 2000 (VPR 332) and Biacore 3000 (VPR 696) (Biacore, Inc., Piscataway, N.J.). The conditions utilized were as described in Mach et al. (*J. Pharm. Sci.* 95: 2195-2206 (2006)), with modifications.

Samples were incubated for 2 months at 2-8° C. prior to sample treatment by aluminum dissolution, followed by the final Biacore analysis. The Biacore results indicated that the preservatives tested had no significant impact on the bioactivity of HPV Type 18 VLPs (data not shown). All results were within the variability of the assay (+/−15% maximum) with the exception of methylparaben/propylparaben (77% average relative in vitro antigenicity, n=2) and thimerosal (80% average relative in vitro antigenicity, n=2).

EXAMPLE 10

Interaction of Preservatives with Aluminum and IMX Glass Vials, and Stoppers

Analysis of preservative stability was performed using reverse phase (RP)-high pressure liquid chromatography (HPLC), as described in Dunn et al. (*J. Pharm Sci* 72: 277-80 (1983)). This method was used to evaluate possible interactions of preservatives with aluminum adjuvants, glass containers, and stoppers.

The results showed that there was no detectable loss of the preservatives after contacting the aluminum adjuvant (data not shown). These results were consistent with our previous studies, which demonstrated that the preservatives tested do not bind to MAA. These studies also demonstrated that IMX does not affect preservative concentration or HPV stability.

Similar studies were performed with glass vials (data not shown) and stoppers.

The compatibility of the preservatives with Teflon-coated stoppers (FluoroTec®, West Pharmaceutical Services, Inc., Lionville, Pa.) was assessed with four different preservatives in HPV formulation buffer. The formulations tested included final concentrations of 1.2% benzyl alcohol, 0.5% phenol, 0.5% chlorobutanol, or 0.3% m-cresol. Each sample was filled at a volume of 0.75 mL into two 3 mL glass vials with FluoroTec®-coated stoppers. The vials were stored at room temperature for 6 months with one vial inverted and another upright. The concentrations of the preservatives were measured using the RP-HPLC method described above.

The results indicate that no preservative loss was detected after 6 months of storage at room temperature for those samples in contact with the stoppers. These results demonstrate that the preservatives do not interact with or adsorb to FluorTec®-coated stoppers in HPV formulation buffer.

The RP-HPLC method was also used for evaluating preservative stability in HPV vaccine formulations. A short-term preliminary study showed that the selected preservatives were fairly stable when the HPV vaccine was stored at 2-8° C. (data not shown). More detailed evaluations with long-term stability studies are described in EXAMPLE 11-12.

EXAMPLE 11

Evaluation of Stability of HPV Vaccine Formulations: Materials and Methods

Based on the initial data obtained from AME, DSC, and Biacore analyses (EXAMPLES 7-9), five preservative-containing formulations (1.2% and 0.9% benzyl alcohol, 0.5% chlorobutanol, 0.3% m-cresol, and 0.5% phenol) were selected for further analysis in long-term stability studies. Several HPV vaccine formulations with various dose and combinations of preservatives, in the presence or absence of IMX adjuvant, were tested.

Each type of HPV VLP aqueous bulk was absorbed on MAA separately with a protein-to-adjuvant ratio of 0.71 to form the monovalent vaccines in 0.32 M NaCl, 10 mM Histidine (pH 6.2), 0.01% (w/v) PS-80. The eight individual monovalent vaccines were then blended together to obtain protein concentrations of 40, 80, 80, 40, 40, 40, 40 and 40 mcg/mL for HPV Types 6, 11, 16, 18, 31, 45, 52, and 58, respectively. This combination formed the octavalent vaccine.

In addition, some formulations contained Isocomatrix® (IMX, CSL Ltd., Parkville, Australia) adjuvant. Stock IMX was prepared in HPV vaccine buffer (described above). IMX was then added to the octavalent vaccine to a final concentration of 240 mcg/mL using a settle-decant procedure to form the octavalent HPV vaccine containing IMX adjuvant. The formulations were gently mixed and stored at 4° C. overnight. The initial preservative screening (EXAMPLE 7) used 120 mcg/mL IMX in the chlorobutanol formulation because the final IMX concentration had not been determined when these experiments were performed.

The formulations were filled at a volume of 0.75 mL in 3 mL glass vials with Teflon-coated stoppers (FluoroTec®, West Pharmaceuticals, Lionville, Pa.) and stored in controlled thermal units at 2-8, 25, 30, and 37° C. prior to testing. The formulation and fill processes were performed under aseptic conditions. For the formulations stored at 2-8° C., the measurements are scheduled to be at 0, 8, 12, 24, and 36 months for preservative, HPV VLP, and IMX adjuvant testing.

EXAMPLE 12

Evaluation of Stability of HPV Vaccine Formulations: Preservative Effectiveness by AME Testing Formulations from the real-time study (2-8° C.) were first evaluated at time 0 for preservative effectiveness using AME testing. The formulations containing 0.5% chlorobutanol and 0.3% m-cresol in the presence or absence of IMX passed the USP, EP-B and EP-A tests. The formulation containing 1.2% benzyl alcohol without IMX passed USP, EP-B, and EP-A, but did not pass EP-A in the IMX-containing formulation. Formulations that did not pass EP-A in the presence or absence of IMX also included 0.9% benzyl alcohol and 0.5% phenol. 3.3.3. Stability Data for 8 Months Storage at 2-8° C. and 3 Months at 30 and 37° C.

The stability of multi-dose, preservative-containing samples was evaluated using in vitro antigenicity (Biacore) for HPV VLPs, and RP-HPLC for preservative and IMX stability.

Figure 7A:
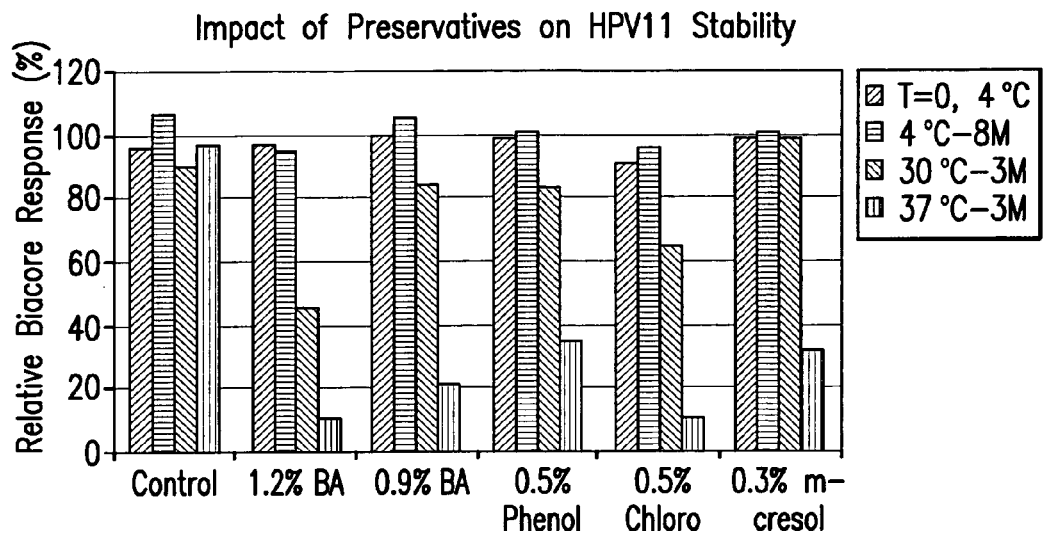
FIG. 7 shows the impact of preservatives on the stability of octavalent HPV vaccine formulations in the absence of IMX (see EXAMPLE 12).
Figure 7B:
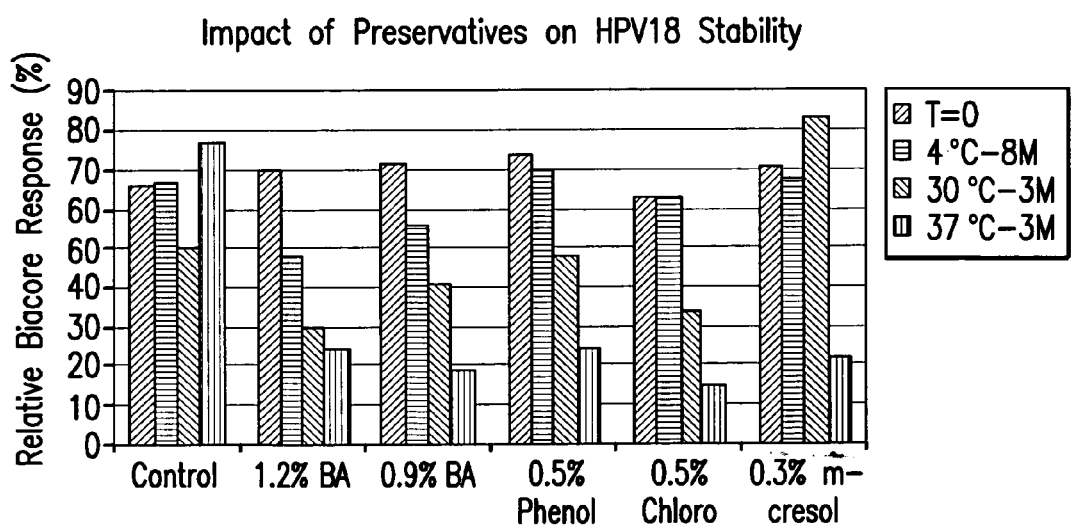
Figure 8A:
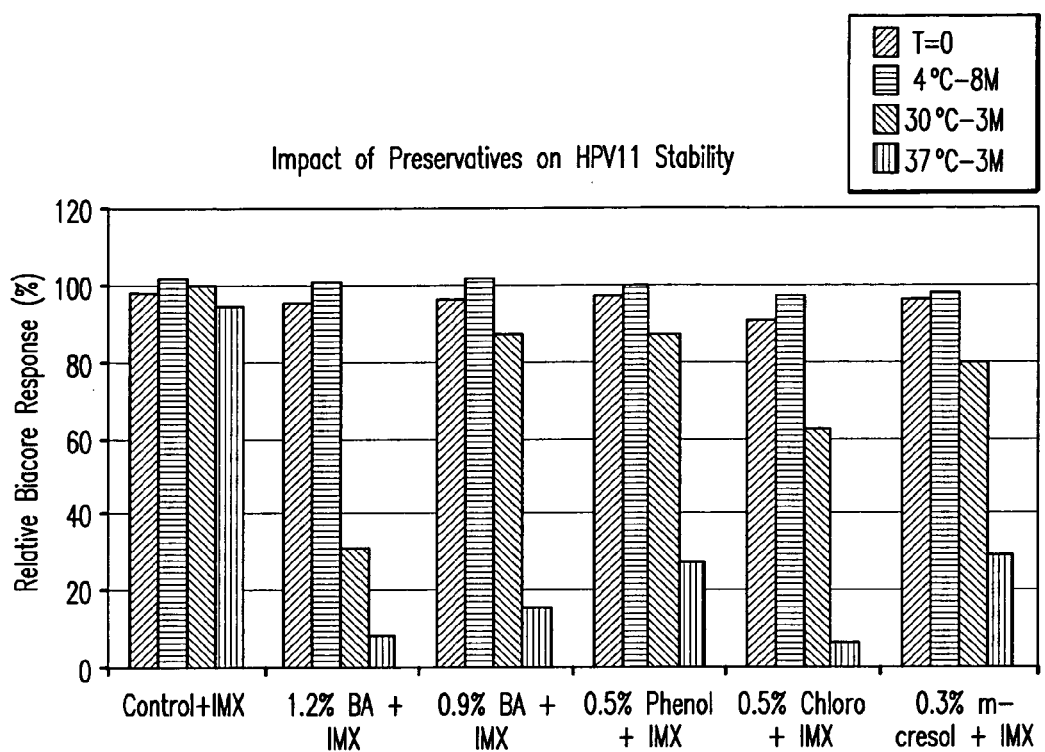
FIG. 8 shows the impact of preservatives on the stability of octavalent HPV vaccine formulations in the presence of IMX (see EXAMPLE 12).
Figure 8B:
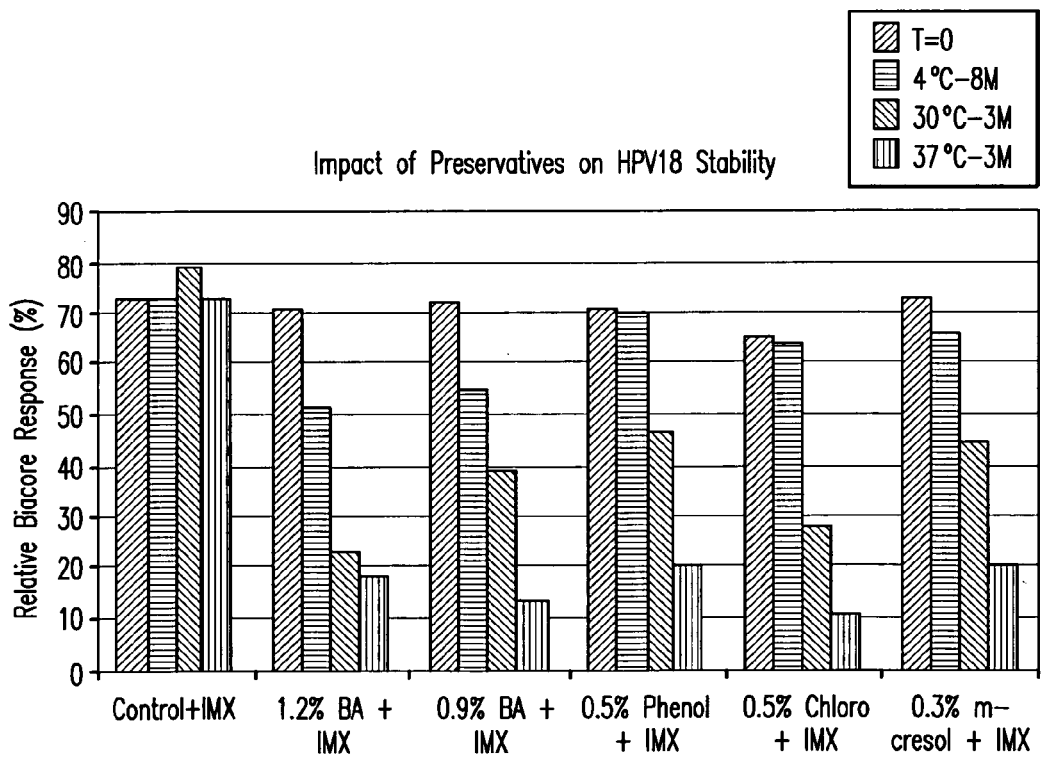

The data from the accelerated stability studies (FIGS. 7 and 8) indicated that all preservatives had a negative impact on the stability of octavalent HPV vaccines at 30 and/or 37° C. However, when the formulations were stored at 2-8° C., the preservatives showed no significant impact on HPV vaccine stability even after 8 months of storage (FIGS. 7 and 8). The data also show that the effect of preservatives on HPV vaccine varies with preservative type. The results of the accelerated stability studies at 30° C. indicated that comparing all preservatives tested, 0.3% m-cresol was the most optimal preservative with the minimum impact on the stability of the multi-dose HPV vaccine, while the 1.2% benzyl alcohol and 0.5% chlorobutanol preservatives had the most impact on HPV vaccine stability. Overall, only three preservatives (0.9% benzyl alcohol, 0.5% phenol, and 0.3% m-cresol) had relatively less impact on HPV vaccine stability.

EXAMPLE 13

Figure 9A:
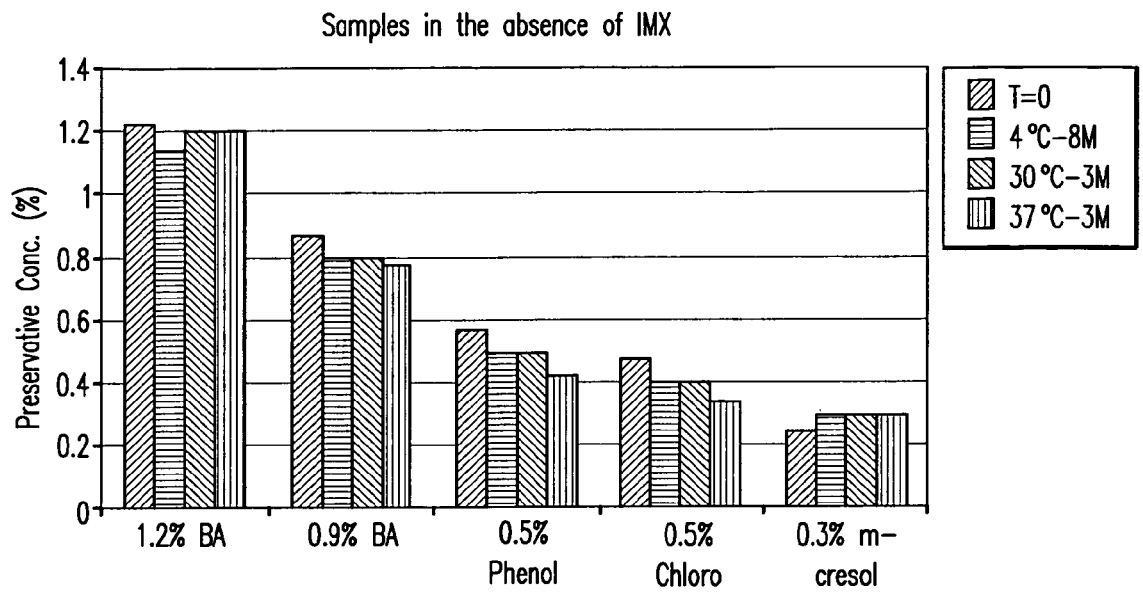
FIG. 9, panel A, shows preservative stability in HPV vaccine formulations in the absence of IMX. Panel B shows preservative stability in HPV vaccine formulations comprising IMX (see EXAMPLE 13).
Figure 9B:
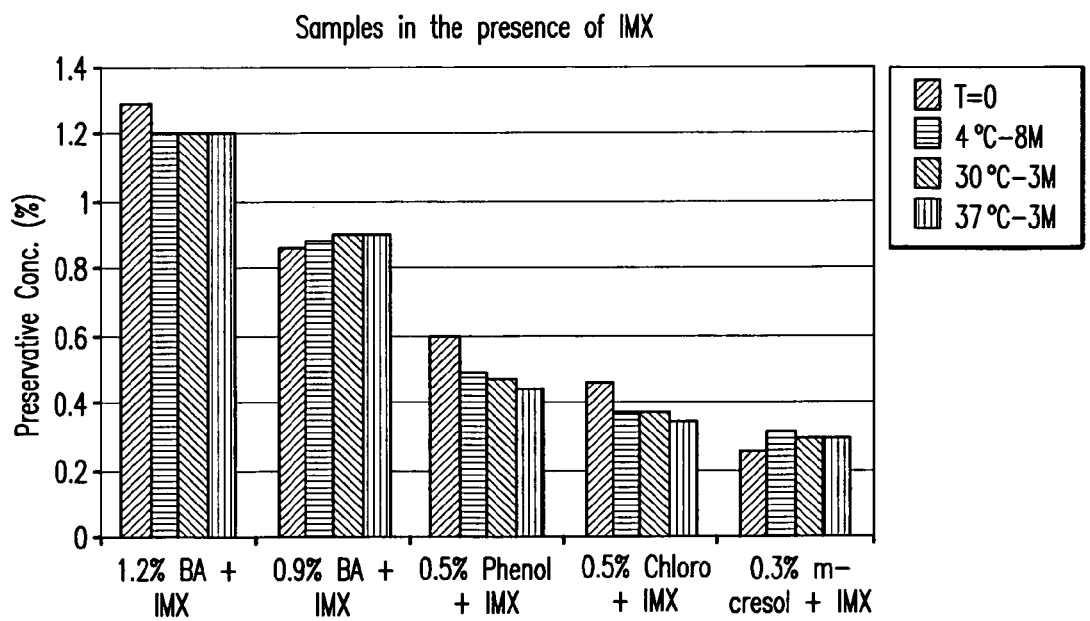

Evaluation of Stability of Preservatives in HPV Vaccine Formulations by RP-HPLC Assay The stability of preservatives in the multi-dose HPV vaccine was monitored by RP-HPLC analysis as previously described (EXAMPLE 10). The results demonstrate that all five preservatives were stable in the multi-dose vaccine formulations in the presence or absence of IMX (FIG. 9). No preservative loss was observed for all formulations tested during this study regardless of storage temperature or duration.

What is claimed:

1. A multi-dose HPV vaccine formulation comprising:
   (a) HPV virus-like particles (VLPs) of at least one HPV type; said HPV VLPs comprised of recombinant L1 or recombinant L1+L2 protein of HPV;
   (b) an aluminum adjuvant; and
   (c) an antimicrobial preservative selected from the group consisting of: m-cresol, phenol, and benzyl alcohol, wherein said HPV VLPs are adsorbed onto said aluminum adjuvant.

2. The multi-dose HPV vaccine formulation of claim 1, wherein the at least one type of HPV VLPs is selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82.

3. The multi-dose HPV vaccine formulation of claim 2, comprising VLPs of HPV types 6, 11, 16, and 18.

4. The multi-dose HPV vaccine formulation of claim 2, comprising VLPs of HPV types 31, 45, 52, and 58.

5. The multi-dose HPV vaccine formulation of claim 2, comprising VLPs of HPV types 31, 35, 45, and 58.

6. The multi-dose HPV vaccine formulation of claim 4, further comprising VLPs of an additional HPV type selected from the group consisting of: HPV26, HPV33, HPV35, HPV39, HPV51, HPV53, HPV55, HPV56, HPV59, HPV66, HPV68, HPV73, and HPV82.

7. The multi-dose HPV vaccine formulation of claim 1, wherein the aluminum adjuvant is selected from the group consisting of: aluminum hydroxyphosphate ($AlPO_4$), amorphous aluminum hydroxyphosphate sulfate (AAHS), and aluminum hydroxide ($Al(OH)_3$).

8. The multi-dose HPV vaccine formulation of claim 7, wherein the aluminum adjuvant comprises $AlPO_4$ or AAHS, which adjuvant comprises phosphate and aluminum present in a molar ratio of about 0.1 to about 1.1 phosphate (PO4) to aluminum (Al).

9. The multi-dose HPV vaccine formulation of claim 8, wherein the aluminum adjuvant comprises phosphate and aluminum present in a molar ratio of about 0.2 to about 0.5 $PO_{O4}/Al$.

10. The multi-dose HPV vaccine formulation of claim 1, wherein the antimicrobial preservative consists of m-cresol at a concentration of about 0.15 to about 0.31%, phenol at a concentration of about 0.25 to about 0.55%, or benzyl alcohol at a concentration of about 0.75 to about 12%.

11. The multi-dose vaccine formulation of claim 10, wherein the antimicrobial preservative consists of m-cresol at a concentration of about 0.3%, phenol at a concentration of about 0.5% or benzyl alcohol at a concentration of about 0.9%.

12. The multi-dose vaccine formulation of claim 10, wherein the antimicrobial preservative is m-cresol at a concentration of about 0.15 to about 0.31%.

13. The multi-dose vaccine formulation of claim 10, wherein the antimicrobial preservative is phenol at a concentration of about 0.25 to about 0.55%.

14. The multi-dose vaccine formulation of claim 10, wherein the antimicrobial preservative is benzyl alcohol at a concentration of about 0.75 to about 1.2%.

15. The multi-dose vaccine formulation of claim 10, further comprising ISCOMATRIX® adjuvant.

16. The multi-dose vaccine formulation of claim 15, wherein the ISCOMATRIX® adjuvant is present at a concentration between 20 μg/ml and 400 μg/ml.

* * * * *